(12) United States Patent
Goel et al.

(10) Patent No.: US 8,686,028 B2
(45) Date of Patent: Apr. 1, 2014

(54) SUBSTITUTED BENZFUROCHROMENES AND RELATED COMPOUNDS FOR THE PREVENTION AND TREATMENT OF BONE RELATED DISORDERS

(75) Inventors: Atul Goel, Lucknow (IN); Amit Kumar, Lucknow (IN); Sumit Chaurasia, Lucknow (IN); Divya Singh, Lucknow (IN); Abnish Kumar Gautam, Lucknow (IN); Rashmi Pandey, Lucknow (IN); Ritu Trivedi, Lucknow (IN); Man Mohan Singh, Lucknow (IN); Naibedya Chattopadhyay, Lucknow (IN); Lakshmi Manickavasagam, Lucknow (IN); Girish Kumar Jain, Lucknow (IN); Anil Kumar Dwivedi, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/127,913

(22) PCT Filed: May 14, 2009

(86) PCT No.: PCT/IN2009/000285
§ 371 (c)(1),
(2), (4) Date: Sep. 15, 2011

(87) PCT Pub. No.: WO2010/052734
PCT Pub. Date: May 14, 2010

(65) Prior Publication Data
US 2012/0003273 A1 Jan. 5, 2012

(30) Foreign Application Priority Data
Nov. 6, 2008 (IN) .......................... 2511/DEL/2008

(51) Int. Cl.
*A61K 31/352* (2006.01)
*A61K 31/4453* (2006.01)
*C07D 311/36* (2006.01)
*C07D 493/04* (2006.01)

(52) U.S. Cl.
USPC ........... 514/453; 514/456; 514/321; 549/383; 549/279; 549/403; 546/197

(58) Field of Classification Search
USPC ........... 424/400; 514/453, 321, 456; 549/383, 549/279, 403; 546/197
See application file for complete search history.

(56) References Cited

FOREIGN PATENT DOCUMENTS

| WO | 2004/080474 A1 | 9/2004 |
| WO | 2006/007503 A1 | 1/2006 |
| WO | 2007/099432 A2 | 9/2007 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Database Beilstein Beilstein Institute for Organic Chemistry, Frankfurt-Main, DE; XP002540048 Database accession No. BRN: 1292487 abstract & Journal of the Chemical Society Perkin Transaction 1: Organic and Bio-Organic Chemistry, vol. 7, 1992, pp. 839-850.

(Continued)

*Primary Examiner* — Kristin Vajda
(74) *Attorney, Agent, or Firm* — Ladas & Parry LLP

(57) ABSTRACT

The present invention relates to novel substituted benzfurochromenes and related compounds having the general formula (I), salts and chiral, achiral derivatives thereof; wherein $R^1, R^2, R^3, R^4, R^5, R^6, R^7, R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro but not limited to this; wherein $R^1R^2$ or $R^2R^3$ or $R^6R^7$ may be connected and form either a five membered ring or a six membered ring such as optionally substituted furan, optionally substituted dihydrofuran, optionally substituted pyran; or may be connected through a methylenedeoxy moiety; wherein X is selected from the units consisting of optionally a ketone group, optionally a methylene group, optionally substituted methylene group, optionally substituted alkene; wherein Y and Z is selected from the units consisting of CH, C—OH, C-Me, C—OMe with the proviso that bond between Y and Z is a single bond; Wherein Y and Z may be a carbon atom with the proviso that bond between Y and Z is a double bond. The compounds of the general formula is useful for the prevention and treatment of bone related disorders.

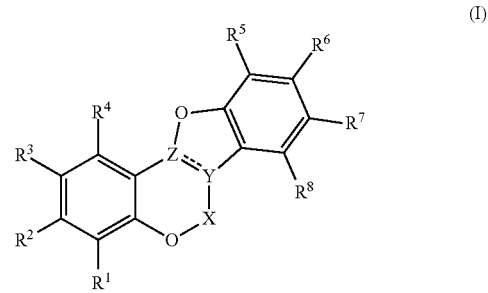

(I)

12 Claims, 9 Drawing Sheets

(56) References Cited

OTHER PUBLICATIONS

Database Beilstein Beilstein Institute for Organic Chemistry, Frankfurt-Main, DE; XP002540043 Database accession No. BRN: 5053756 abstract & Journal of the Chemical Society Perkin Transaction 1: Organic and Bio-Organic Chemistry, 1981, pp. 2684-2691.
D.H. Marshall, et al; "The prevention and management of post-menopausal osteoporosis", Acta Obstet Gynecol Scan. Suppl. Jan. 1977, vol. 65, 3 pages, Abstract Only.
Michael E. Mendelsohn, et al; "Estrogen and the blood vessel wall", Current Opinion in Cardiology, Sep. 1994, vol. 9, Issue 5, 2 pages, Abstract Only.
P.M. Dewich-Harborne, J.B., Ed.: The Flavonoids: Advances in Research Since 1986; Book Chapman and Hall: London, 1994; 3 pages.
Stephen M. Berge, et al. "Pharmaceutical Salts", Journal of Pharmaceutical Sciences, Jan. 1977, vol. 66, No. 1, pp. 1-19.
Rogerio A. Lobo MD; "Cardiovascular Implications of Estrogen Replacement Therapy", Obstetrics & Gynecology, Apr. 1990, vol. 75, Issue 4, 2 pages, Abstract Only.
Patricia Maximo, et al; "A Pterocarpan From *Ulex parviflous*", Phytochemistry, vol. 48, No. 2, pp. 359-362, 1998.
Hitoshi Tanaka, et al; "Isoflavanoids from the roots of *Erythrina poeppigiana*" Phytochemistry, vol. 60, Aug. 2002, pp. 789-794.
Meir J. Stampfer, M.D., et al; "Estrogen Replacement Therapy and Coronary Heart Disease: A Quantitative Assessment of the Epidemiologic Evidence[1,2]", Preventive Medicine vol. 20, pp. 47-63 1991.
Dawn R. Perrin; "The Structure of Phaseolin", Tetrahedron Letters No. 1, pp. 29-35, 1964.
Masashi Nakagawa, et al; "Structures of Cabenegrins A-I and A-II, Potent Anti-Snake Venoms", Tetrahedron Letters, vol. 23, No. 38, pp. 3855-3858, 1982.
Tom A. Hutchinson, et al; "Post-Menopausal Oestrogens Protect Against Fractures of Hip and Distal Radius A Case-control Study", The Lancet, Saturday Oct. 6, 1979; pp. 705-709.
International Search Report; mailed Aug. 14, 2009; PCT/IN2009/000285.
Suresh Awale, et al; "Constituents of Brazilian red propolis and their preferential cytotoxic activity against human pancreatic PANC-1 cancer cell line in nutrient-deprived condition", Bioorganic & Medicinal Chemisty, vol. 16, pp. 181-189, Available online Oct. 5, 2007.
Feng Li, et al; "Cytotoxic constituents from Brazilian red propolis and their sructure-activity relationship", Bioorganic & Medicinal Chemistry, vol. 16, pp. 5434-5440, Available online Apr. 12, 2008.
XP-002540044; Beilstein Registry No. 1253603; 3-Hydroxy-bepzo[4,5]uro[3,2-c]chromen-6-one; 3 pages; Feb. 2009; Beilstein Database.
XP-002540045; Beilstein Registry No. 251390; 7-hydroxy-3-(2-methoxy-phenyl)-chromen-4-one; 23 pages; Feb. 2009 Beilstein Database.
XP-002540046; Beilstein Registry No. 224494; 7-Hydroxy-3-(2-hydroxy-phenyl)-chromen-4-one; 5 pages; Feb. 2009; Beilstein Database.
XP-002540047; Beilstein Registry No. 1295070; 3-(2,4-Dimethoxy-phenyl)-7-hydroxy-chromen-4-one; 8 pages; Feb. 2009; Beilstein Database.

* cited by examiner

General Formula I

Template I

Template II

Scheme 1

SUBSTITUTED BENZFUROCHROMENES AND RELATED COMPOUNDS FOR THE PREVENTION AND TREATMENT OF BONE RELATED DISORDERS

FIELD OF THE INVENTION

The present invention relates to the development of substituted benzfurochromenes and related compounds of the general formula I showing in the drawing accompanying the specifications, which can be used as therapeutic agents for the prevention or treatment of various medical indications associated with estrogen independent or dependent diseases or syndromes preferably in prevention or treatment of diseases and syndromes caused in humans and animals.

The present invention more particularly relates to a compound of formula I:

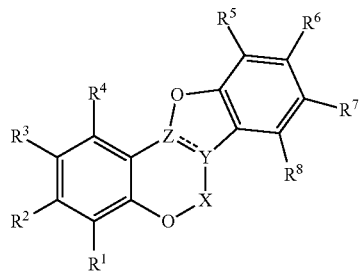

Wherein $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro but not limited to this;

Wherein $R^1R^2$ or $R^2R^3$ or $R^6R^7$ may be connected and form either a five membered ring or a six membered ring such as optionally substituted furan, optionally substituted dihydrofuran, optionally substituted pyran; or may be connected through a methylenedeoxy moiety;

Wherein X is selected from the units consisting of optionally a ketone group, optionally a methylene group, optionally substituted methylene group, optionally substituted alkene;

Wherein Y and Z is selected from the units consisting of CH, C—OH, C-Me, C—OMe with the proviso that bond between Y and Z is a single bond;

Wherein Y and Z may be a carbon atom with the proviso that bond between Y and Z is a double bond;

More particularly, the present invention relates to optionally substituted benzfurochromenes, and their related compounds, processes for preparing the said compounds and their pharmaceutically acceptable salts and compositions that are useful for the prevention or treatment of various medical indications associated with estrogen independent or dependent diseases or syndromes preferably in prevention or treatment of diseases and syndromes caused in humans and animals in particular: Osteoporosis, bone loss, bone formation; bone formation during Type-Wage related/senile osteoporosis, period of development and growth to attain higher peak bone mass, bone fracture healing, promotion of new bone formation in vitro/in vivo for replacement of defective bone; estrogen related diseases or syndromes, preferably diseases or syndromes caused by an estrogen-deficient state in a mammal; cardiovascular effects more particularly hyperlipidaemia, thrombosis and vasomotor system; neurodegenerative effects such as stroke, senile dementia-Alzheimer type and Parkinson disease; menopausal symptoms including hot flushes, urogenital atrophy, depression, mania, schizophrenia and the like, urinary incontinence, relief of dysmenorrhea; relief of dysfunctional uterine bleeding, an aid in ovarian development, treatment of acne and hirsutism; cancers such as prostatic carcinoma, cancer of breast, cancer of uterus, cancer of the cervix and cancer of the colon; control or regulation of fertility in humans and in other animals; for use in the prevention of threatened or habitual abortion; suppression of post-partum lactation; physiological disorders such as obesity, depression etc.;

BACKGROUND OF THE INVENTION

Osteoporosis, which has been defined as a "state of low bone mass", is one of the major problems in our aging society. It is a disease characterized by micro architectural deterioration of bone tissue leading to enhanced bone fragility and consequent increase in fracture risk in older members of the population. It is known to affect >50% of women and 30% men over the age of 50 years. In women, there is also an accelerated rate of bone loss immediately and for variable number of years following menopause.

Efforts to reduce this risk factor and incidence of fractures have resulted in the development of compounds that conserve skeletal mass by inhibiting bone resorption and/or by enhancing bone formation (Dwivedy I, Ray S, 1995 "Recent developments in the chemotherapy of osteoporosis" Progress in Drug Research 45, 289-338, Editor E Jucker, Birkhauser Vela; Marshall D H, Horsmann A, Nordin B E C, 1977, "The prevention and management of post-menopausal osteoporosis" Acta Obstet Gynecol Scand (Suppl) 65:49-56; Hutchinson T A, Polansky S M, Feinstein A R, 1979, "Postmenopausal estrogen protect against fractures of hip and distal radius: A care-control study" Lancet 2:705-709. Estrogen replacement therapy also has positive effect on CVS & CNS related disorders (Lobo R A, 1990, "Cardiovascular implication of estrogen replacement therapy" Obstetrics & Gynaecology 75:185-245; Mendelson M E, Karas R H, 1994, "Estrogen and the blood vessel wall" Current opinion in Cardiology 1994:619-626; Stampfer M J, Colditz G A, 1991, "Estrogen replacement therapy and coronary heart disease: a quantitative assessment of the epidemiological evidence" Preventive Medicine 20:47-63).

Most of the pharmacological agents available for clinical use such as calcium, vitamin D and its analog, estrogen, calcitonin, bisphosphonates, raloxifene etc. act by decreasing the rate of bone resorption, thereby slowing the rate of bone loss. Timely administration of such antiresorptive agents prevents bone loss. However, bone once lost cannot be recovered by use of such antiresorptive agents.

In traditional medicine, there are many natural crude drugs that have the potential to treat bone diseases. However, not much laboratory work has been reported evaluating their possible development and use, except ipriflavone, an isoflavonoid, which has been used clinically for this indication.

The compounds included in this patent have been demonstrated to promote proliferation and differentiation of osteoblasts, matrix maturation and mineralization in vitro in a number of assays and increase bone mineral density and bone mechanical strength following prolonged treatment in vivo and would be of tremendous use not only in fast fracture healing and management of age-related (Type-II) osteoporosis, but might also help in attaining higher peak bone mass when administered during the period of growth and development, promote new bone formation in vitro/in vivo for replacement of defective bone and prevention of resorption in estrogen deficiency states including post-menopausal osteoporosis. Some of the compounds of the present invention show good systemic availability in experimental animals correlating well with its pharmacodynamic properties.

Currently the only agents reported to show bone formation activity include (a) parathyroid hormone, which is to be administered parenterally and increases bone resorption at higher doses, (b) fluoride, excessive intake of which is also known to cause osteoporosis and (c) androgens by virtue of their anabolic activity. This is the first agent of its kind from natural sources and would be developed as an oral formulation for human use and welfare.

The benzfurochromenes constitute the second largest group of natural isoflavonoids, which contain a tetracyclic ring system derived from the isoflavonoid skeleton by an ether linkage between the 4- and 2'-positions [(a) Dewich, P. M. In Harborne, J. B., Ed.; The Flavanoids: Advances in Research Since 1986; Chapman and Hall: London, 1994; (b) Tanaka, H.; Oh-Uchi, T.; Etoh, H.; Shimizu, H.; Tateishi, Y. Phytochemistry 2002, 60, 789]. Various biological activities are associated with this compound, which include potent phytoalexins (Mansfield, J. W. In Phytoalexins; Bailey, J. A., Mansfield, J. W., Eds.; Glasgow, 1982.), antitoxin and antiviral (Nakagawa, M.; Nakanishi, K.; Darko, L. L.; Vick, J. A. Tetrahedron Lett. 1982, 23, 3855.), antifungal ((a) Maximo, P.; Lourenc, o, A. Phytochemistry 1998, 48, 359; (b) Perrin, D. R. Tetrahedron Lett. 1964, 1, 29.), and antibacterial (Ingham, J. L. In Progress in the Chemistry of Organic Natural Products; Herz, W., Grisebach, H., Kirby, G. W., Eds.; Springer: New York, 1983; Vol. 43, pp 1-266.) properties. We are involved in the synthesis of natural products such as flavonoids, terpenes and other related biologically important oxygen heterocycles and evaluate their biological properties in various in-house screening models. Recently we prepared a series of benzfurochromenes and related compounds for the prevention or treatment of various medical indications associated with estrogen independent or dependent diseases or syndromes preferably in prevention or treatment of diseases and syndromes caused in humans and animals, in particular: Osteoporosis, bone loss, bone formation; bone formation during Type-II/age related/senile osteoporosis, period of development and growth to attain higher peak bone mass, bone fracture healing, promotion of new bone formation in vitro/in vivo for replacement of defective bone.

Some of the novel synthesized benzfurochromenes particularly 3-allyloxy-4-methyl-6a,11a-dihydro-6H-benzo[4,5]furo[3,2-c]chromene (S-007-1500) showed stimulation in ALP activity in calvarial derived osteoblasts from $10^{-12}$M to $10^{-6}$M concentrations in repeated screening. Such encouraging results prompted us to prepare several nature-mimicking benzfurochromenes and their related compounds for the prevention or treatment of various medical indications associated with estrogen independent or dependent diseases or syndromes preferably in prevention or treatment of diseases and syndromes caused in humans and animals. The detailed biological studies (in vitro and in vivo) on the synthesized compounds are mentioned in biological evaluation section of the draft.

Osteoporosis is one of the major problems in our aging society. Osteoporosis results in bone fracture in older members of the population, especially in post-menopausal women. In traditional medicine, there are many natural crude drugs that have the potential for use to treat bone diseases. So far, there is no drug available which show osteogenic and anti-osteoclastogenic activity. Therefore, there is an urgent need to discover and develop a drug, which possess the ideal pharmacological profile and promote new bone formation.

OBJECTS OF THE INVENTION

The main object of the present invention is to provide the substituted benzfurochromenes and related compounds for the prevention and treatment of bone related disorders.

Another object of the present invention is to provide a process for preparation of substituted benzfurochromenes and related compounds.

Still another object of the invention is to provide the compounds to have bone forming/strengthening activity.

SUMMARY OF THE INVENTION

Accordingly, the present invention provides substituted novel benzfurochromenes and related compounds having the general formula I, salts and chiral, achiral derivatives thereof;

General formula I

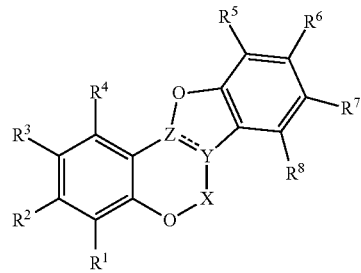

wherein $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro but not limited to this;
wherein $R^1R^2$ or $R^2R^3$ or $R^6R^7$ may be connected and form either a five membered ring or a six membered ring such as optionally substituted furan, optionally substituted dihydrofuran, optionally substituted pyran; or may be connected through a methylenedeoxy moiety;
wherein X is selected from the units consisting of optionally a ketone group, optionally a methylene group, optionally substituted methylene group, optionally substituted alkene;
wherein Y and Z is selected from the units consisting of CH, C—OH, C-Me, C—OMe with the proviso that bond between Y and Z is a single bond;
Wherein Y and Z may be a carbon atom with the proviso that bond between Y and Z is a double bond;
In an embodiment of the present invention wherein the especially preferred novel compounds having the general formula I are more specifically described by Template I;

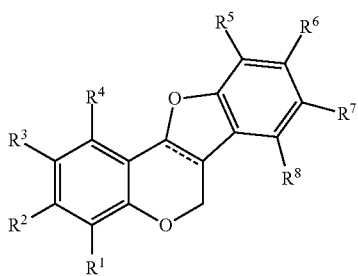

Template-I wherein $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro but not limited to this; wherein $R^1R^2$ or $R^2R^3$ or $R^6R^7$ may be connected and may form either a five membered ring or a six membered ring such as optionally substituted furan, optionally substituted dihydrofuran, optionally substituted pyran; or may be connected through a methylenedeoxy moiety;

In another embodiment of the present invention wherein the novel precursors of the compounds having the general formula of Template-I are specifically described by Template II;

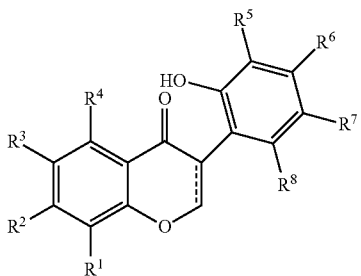

Template-II wherein $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro but not limited to this; wherein $R^1R^2$ or $R^2R^3$ or $R^6R^7$ may be connected and may form either a five membered ring or a six membered ring such as optionally substituted furan, optionally substituted dihydrofuran, optionally substituted pyran; or may be connected through a methylenedeoxy moiety.

In yet another embodiment of the present invention wherein the representative compounds comprising the following, but not limited to these examples;
  i. 3-Allyloxy-4-methyl-6a,11a-dihydro-6H-benzo[4,5]furo[3,2-c]chromene
  ii. 4-Methyl-6a,11a-dihydro-6H-benzo[4,5]furo[3,2-c]chromen-3-ol
  iii. 6a,11a-Dihydro-6H-benzo[4,5]furo[3,2-c]chromen-3-ol
  iv. (4-Methyl-6a,11a-dihydro-6H-benzo[4,5]furo[3,2-c]chromen-3-yloxy)-acetonitrile
  v. 3-isopropoxy-6a,11a-dihydro-6H-benzofuro[3,2-c]chromene
  vi. 3-(allyloxy)-6a,11a-dihydro-6H-benzofuro[3,2-c]chromene
  vii. 1-(2-(6a,11a-dihydro-6H-benzofuro[3,2-c]chromen-3-yloxy)ethyl)piperidine
  viii. 3-hydroxy-6H-benzofuro[3,2-c]chromen-6-one
  ix. 7,8-Dihydroxy-3-(2-methoxy-phenyl)-chromen-4-one
  x. 7,8-Dihydroxy-3-(2-hydroxy-phenyl)-chromen-4-one
  xi. 6-Chloro-7-hydroxy-3-(2-methoxy-phenyl)-chromen-4-one
  xii. 6-Chloro-7-hydroxy-3-(2-hydroxy-phenyl)-chromen-4-one
  xiii. 7-Hydroxy-3-(2-hydroxy-phenyl)-8-methyl-chromen-4-one
  xiv. 7-Hydroxy-3-(2-methoxy-phenyl)-chromen-4-one
  xv. 7-Hydroxy-3-(2-hydroxy-phenyl)-chromen-4-one
  xvi. 3-(2,4-Dimethoxy-phenyl)-7-hydroxy-chromen-4-one
  xvii. 7-Hydroxy-3-(2-hydroxy-4-methoxy-phenyl)-chromen-4-one In a further embodiment of the present invention wherein the compounds are useful for the prevention or treatment of various medical indications associated with estrogen independent or dependent diseases or syndromes preferably in prevention or treatment of diseases and syndromes caused in humans and animals in particular: osteoporosis, bone loss, bone formation; bone formation during Type-II/age related/senile osteoporosis, period of development and growth to attain higher peak bone mass, bone fracture healing, promotion of new bone formation in vitro/in vivo for replacement of defective bone; estrogen related diseases or syndromes, preferably diseases or syndromes caused by an estrogen-deficient state in a mammal; cardiovascular effects more particularly hyperlipidaemia, thrombosis and vasomotor system; neuro-degenerative effects such as stroke, senile dementia-Alzheimer type and Parkinson disease; menopausal symptoms including hot flushes, urogenital atrophy, depression, mania, schizophrenia and the like, urinary incontinence, relief of dysmenorrhea; relief of dysfunctional uterine bleeding, an aid in ovarian development, treatment of acne and hirsutism; cancers such as prostatic carcinoma, cancer of breast, cancer of uterus, cancer of the cervix and cancer of the colon; control or regulation of fertility in humans and in other animals; for use in the prevention of threatened or habitual abortion; suppression of post-partum lactation; physiological disorders such as obesity, depression. In an embodiment of the present invention wherein the compounds showed significant increase in the mineralization of nascent calcium deposition over control at $10^{-12}$ M and $10^{-10}$ M in 18 d bone marrow culture.

In an embodiment of the present invention wherein the compounds showed osteoblast ALP activity at a concentration ranging from $10^{-12}$M to $10^{-6}$M.

In an embodiment of the present invention wherein the compounds significantly inhibited adipogenesis at different concentrations i.e. $10^{-12}$M to $10^{-10}$M.

In an embodiment of the present invention wherein the compounds significantly increases BMD in vivo at a dose ranging between 1.0 and 10 mg/kg.

In a further embodiment of the present invention the compounds of formula I salts and chiral, achiral derivatives thereof,

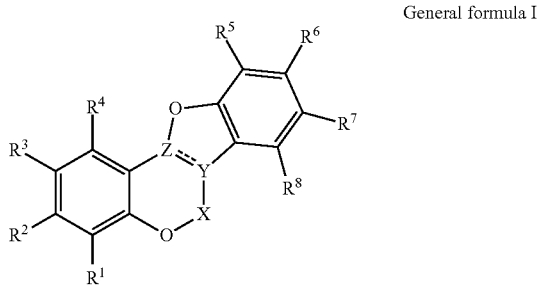

General formula I

Wherein $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro but not limited to this;

Wherein $R^1R^2$ or $R^2R^3$ or $R^6R^7$ may be connected and form either a five membered ring or a six membered ring such as optionally substituted furan, optionally substituted dihydrofuran, optionally substituted pyran; or may be connected through a methylenedeoxy moiety;

Wherein X is selected from the units consisting of optionally a ketone group, optionally a methylene group, optionally substituted methylene group, optionally substituted alkene;

Wherein Y and Z is selected from the units consisting of CH, C—OH, C-Me, C—OMe with the proviso that bond between Y and Z is a single bond;

Wherein Y and Z may be a carbon atom with the proviso that bond between Y and Z is a double bond;

Wherein all the known natural and synthetic pterocarpan class of compounds such as 6a,11a-dihydro-6H-benzo[4,5]furo[3,2-c]chromen-3-ol (S-006-1709) but not limited to this compound and novel isoflavone and related compounds are useful for the treatment of osteoporosis, bone loss, bone formation; bone formation during Type-II/age related/senile osteoporosis, period of development and growth to attain higher peak bone mass, bone fracture healing or any other bone disorders.

Accordingly, the present invention relates to a process of preparing substituted benzfurochromenes and related compounds having the general formula I, salts and derivatives thereof as claimed in claim 1 comprising;

(i) reacting compound having general formula A with substituted 2'-methoxyphenyl acetic acid of formula B in the presence of Lewis acid preferably borontrifluoride etherate at a temperature ranging between 25° C. to 150° C. for a period ranging between 1 hr to 20 hr, as shown in drawing accompanying the specification wherein the substituents $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro etc.;

(ii) isolating the compound of general formula C as shown in drawing accompanying the specification and purifying the compound of formula C by chromatographic techniques;

(iii) reacting compound of general formula C with methanesulfonyl chloride in the presence of acidic medium and heating at a temperature ranging between 25° C. to 100° C. for a period ranging between 1 to 10 hr, (iv) isolating the compound of general formula D as shown in drawing accompanying the specification wherein the substituents $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro etc.; purifying the compound of formula D by chromatographic techniques;

(v) reacting compound of general formula D with either boron tribromide or aluminium trichloride in protic or aprotic solvents selected form a group consisting of THF, DMF, ethanol, acetonitrile, dichloromethane etc. at a temperature ranging between −40° C. to 150° C. for a period ranging between 1 to 20 hr, wherein the substituents $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro etc.; isolating and purifying the compound of formula E by chromatographic techniques;

(vi) reacting compound of general formula E with reducing agents such as lithium aluminum hydride, sodium borohydride in a protic or aprotic solvent like DMSO, ethanol, methanol, THF, DMF etc. at a temperature ranging between 0° C. to 150° C. for a period ranging between 1 to 20 hr, as shown in drawing accompanying the specification wherein the substituents $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride, nitro, isolating and purifying the compound of formula F by chromatographic techniques.

In an embodiment of the present invention wherein the compounds may be converted to the pharmaceutically acceptable salts comprising of hydrochloride, formate, acetate, phenyl acetate, trifluoroacetate, acrylate, ascorbate, benzoate, chlorobenzoates, bromobenzoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumarate, heptanoate, hippurate, lactate, malate, maleate, malonate, nicotinate, isonicotinate, oxalate, sodium, potassium, phthalate, terephthalate, phosphate, monohydrogen phosphate, dihydrogen phosphate, metaphosphate, pyrophosphate, propiolate, propionate, phenylpropionate, salicylate, sebacte, succinate, suberate, sulphate, bisulphate, pyrosulphate, sulphite, bisulphate, sulphonate, benzene sulphonate, bromobenzene sulphonates, chlorobenzene sulphonates, ethane sulphonates, methane sulphonates, naphthalene sulphonates, toluene sulphonates, and the likes.

A pharmaceutical composition comprising the compounds of general formula I or pterocarpans such as 6a,11a-dihydro-6H-benzo[4,5]furo[3,2-c]chromen-3-ol (S-006-1709), along with or without pharmaceutically acceptable carrier(s) or diluent(s) or excipient(s) for prevention or treatment of diseases and syndromes caused by osteoporosis, bone loss, bone formation, bone fracture healing, attainment of higher peak bone mass when administered during the period of growth, and promotion of new bone formation.

In an embodiment of the invention wherein the ratio of the compound of formula I or pterocarpans such as 6a,11a-Dihydro-6H-benzo[4,5]furo[3,2-c]chromen-3-ol (S-006-1709), and pharmaceutically acceptable carrier(s) or diluent(s) or excipient(s) is preferably ranging between 1-20% of the core material with 10-40% of non-ionic surfactant for each mg of drug loading followed by encapsulation with 10-60% of polyelectrolytes with opposite charges and 10-30% of bile salts for surface modification.

The pharmaceutically acceptable salts of the general formula and compositions that are useful for the prevention or treatment of various medical indications associated with estrogen independent or dependent diseases or syndromes preferably in prevention or treatment of diseases and syndromes caused in humans and animals in particular: Osteoporosis, bone loss, bone formation; bone formation during Type-II/age related/senile osteoporosis, period of development and growth to attain higher peak bone mass, bone fracture healing, promotion of new bone formation in vitro/in vivo for replacement of defective bone; estrogen related diseases or syndromes, preferably diseases or syndromes caused by an estrogen-deficient state in a mammal; cardiovascular effects more particularly hyperlipidaemia, thrombosis and vasomotor system; neurodegenerative effects such as stroke, senile dementia-Alzheimer type and Parkinson disease; menopausal symptoms including hot flushes, urogenital atrophy, depression, mania, schizophrenia and the like, urinary incontinence, relief of dysmenorrhea; relief of dysfunctional uterine bleeding, an aid in ovarian development, treatment of acne and hirsutism; cancers such as prostatic carcinoma, cancer of breast, cancer of uterus, cancer of the cervix and cancer of the colon; control or regulation of fertility in humans and in other animals; for use in the prevention of threatened or habitual abortion; suppression of post-partum lactation; physiological disorders such as obesity, depression etc.

In accordance with the principal embodiment, the present invention provides benzfurochromenes and related compounds, their pharmaceutically acceptable salts and compositions that are useful for the prevention or treatment of various medical indications associated with estrogen independent or dependent diseases or syndromes preferably in prevention or treatment of diseases and syndromes caused in humans and animals.

In an important embodiment, the present invention provides a pharmaceutical composition comprising a therapeutically effective amount of benzfurochromenes and related compounds, their pharmaceutically acceptable salts and compositions thereof, alone, in a mixture form or in a combination of a pharmacologically active or inactive agent or both and one or more pharmaceutically acceptable carrier or excipient.

In another embodiment, the present invention provides a medical method of employing the benzfurochromenes and related compounds, their pharmaceutically acceptable salts and pure compounds isolated from these or other natural sources or synthesized, their pharmaceutically acceptable salts and compositions thereof and methods of using such agents for the prevention or treatment of symptoms of estrogen dependent or independent states in mammals and animals, in particular osteoporosis, bone loss, bone formation and cardiovascular effects and estrogen dependent or estrogen independent cancers and for the treatment of disease conditions or disorders associated with an aberrant physiological response to endogenous estrogen including control or regulation of fertility in humans and in other animals.

In an important embodiment, the present invention demonstrates systemic availability of one of the compounds S006-1709 of the present invention, in experimental animals.

BRIEF DESCRIPTION OF THE DRAWINGS

The present invention may be more clearly understood by reference to the following Figures.

DETAILED DESCRIPTION OF THE INVENTION

Figure 1A:
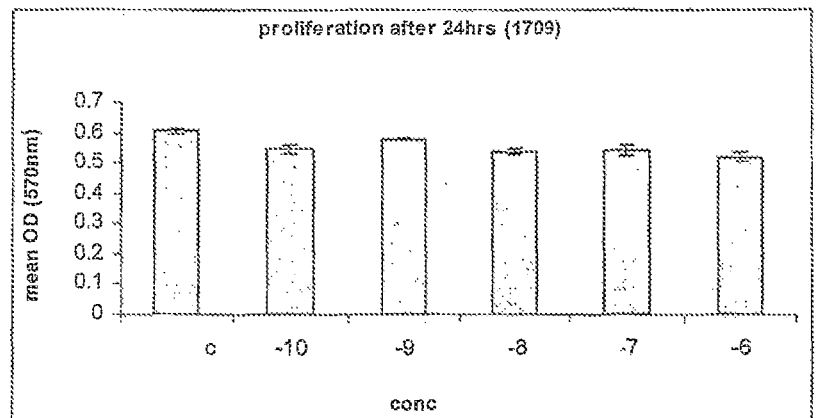
FIG. 1a illustrates the effect of Compound S006-1709 on osteoblast proliferation.

The present invention relates to a compound of formula I:

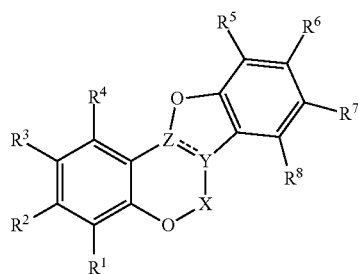

I

Wherein $R^1$, $R^2$, $R^3$, $R^4$, $R^5$, $R^6$, $R^7$, $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride, nitro but not limited to this;

Wherein $R^1R^2$ or $R^2R^3$ or $R^6R^7$ may be connected and form either a five membered ring or a six membered ring such as optionally substituted furan, optionally substituted dihydrofuran, optionally substituted pyran; or may be connected through a methylenedeoxy moiety;

Wherein X is selected from the units consisting of optionally a ketone group, optionally a methylene group, optionally substituted methylene group, optionally substituted alkene;

Wherein Y and Z is selected from the units consisting of CH, C—OH, C-Me, C—OMe with the proviso that bond between Y and Z is a single bond;

Wherein Y and Z may be a carbon atom with the proviso that bond between Y and Z is a double bond, and their pharmaceutically acceptable salts and compositions and methods of using such agents for the prevention or treatment of symptoms of various medical indications associated with estrogen independent or dependent diseases or syndromes caused in humans and/or animals.

The term "pharmaceutically acceptable salts" as used throughout this specification and the appended claims denotes salts of the types disclosed in the article by Berge et al. (J. Pharmaceutical Sciences, 66 (1), 1-19, 1977). Suitable pharmaceutically acceptable salts include salts formed by in-organic acids such as hydrochloric acid, hydrobromic acid, hydroiodic acid, nitric acid, sulphuric acid, phosphoric acid, hypophosphoric acid, and the like, as well as the salts derived from organic acids such as aliphatic mono and dicarboxylic acids, phenyl substituted alkanoic acids, aromatic acids, aliphatic and aromatic sulphonic acids. Such pharmaceutically acceptable acid addition salts include formate, acetate, phenyl acetate, trifluoroacetate, acrylate, ascorbate, benzoate, chlorobenzoates, bromobezoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumarate, heptanoate, hippurate, lactate, malate, maleate, malonate, nicotinate, isonicotinate, oxalate, phthalate, terephthalate, phosphate, monohydrogen phosphate, dihydrogen phosphate, metaphosphate, pyrophosphate, propiolate, propionate, phenylpropionate, salicylate, sebacte, succinate, suberate, sulphate, bisulphate, pyrosulphate, sulphite, bisulphate, sulphonate, benzene sulphonate, bromobenzene sulphonates, chlorobenzene sulphonates, ethane sulphonates, methane sulphonates, naphthalene sulphonates, toluene sulphonates, and the like. Most preferred salts are fumarate or ascorbate or hydrochloride.

The term "pharmaceutically acceptable compositions" of the agents of the present invention as used throughout this specification and the appended claims may be prepared by procedures known in the art using pharmaceutically acceptable excipients known in the art.

Methods of preventing or treating disorders or disease conditions mentioned herein comprise administering to an individual human being or any other mammal or any other animal in need of such treatment a therapeutically effective amount of one or more of the agents of this invention or a pharmaceutically acceptable salt or a pharmaceutically acceptable composition thereof with one or more of the pharmaceutically acceptable carriers, excipients etc.

The dosage regimen and the mode of administration of the agents of this invention or a pharmaceutically acceptable salt or a pharmaceutically acceptable composition thereof with one or more of the pharmaceutically acceptable carriers, excipients etc. will vary according to the type of disorder or disease conditions described herein and will be subject to the judgment of the medical practitioner involved.

The agent of this invention or a pharmaceutically acceptable salt or a pharmaceutically acceptable composition thereof with one or more of the pharmaceutically acceptable carriers, excipients etc. may be effectively administered in doses ranging from 0.1 mg to 5000 mg, more preferably in doses ranging from 0.5 to 1000 mg or still more preferably in the doses ranging from 1 mg to 500 mg weekly or bi-weekly or daily or twice a day or three times a day or in still more divided doses.

Therapeutically effective amounts of agents of the present invention or a pharmaceutically acceptable composition thereof may be enclosed in gelatin capsules or compressed into the tablets or pills or may be formulated in the form of lozenges, inclusion complexes with cyclodextrin derivatives, injectable depo formulations, aerosols, granules, powders, oral liquids, mucosal adhesive formulations, gel formulations, troches, elixirs, suspensions, syrups, wafers, liposomal delivery systems, implants, suppository, pessary, microemulsions, nanoemulsion, microparticles, nanoparticles, controlled release delivery systems, transdermal delivery systems, targeted delivery systems such as conjugates with monoclonal antibodies or with other suitable carrier moieties.

Such doses may be administered by any appropriate route for example, oral, systemic, local or topical delivery for example, intravenous, intra-arterial, intra-muscular, subcutaneous, intraperitoneal, intra-dermal, buccal, intranasal, inhalation, vaginal, rectal, transdermal or any other suitable means in any conventional liquid or solid dosage form to achieve, conventional delivery, controlled delivery or targeted delivery of the compounds of this invention or a pharmaceutically acceptable salt or a pharmaceutically acceptable composition thereof with one or more of the pharmaceutically acceptable carriers, excipients etc.

A preferred mode of administration of agents of the present invention or a pharmaceutically acceptable salt or a pharmaceutically acceptable composition thereof is oral.

Oral compositions will generally comprise of agents of the present invention or a pharmaceutically acceptable composition thereof and one or more of the pharmaceutically acceptable excipients.

The oral compositions such as tablets, pills, capsules, powders, granules, and the like may contain any of the following pharmaceutically acceptable excipients:
1. a diluent such as lactose, mannitol, sorbitol, microcrystalline cellulose, sucrose, sodium citrate, dicalcium phosphate, or any other ingredient of the similar nature alone or in a suitable combination thereof;
2. a binder such as gum tragacanth, gum acacia, methyl cellulose, gelatin, polyvinyl pyrrolidone, starch or any other ingredient of the similar nature alone or in a suitable combination thereof;
3. a disintegrating agent such as agar-agar, calcium carbonate, sodium carbonate, silicates, alginic acid, corn starch, potato tapioca starch, primogel or any other ingredient of the similar nature alone or in a suitable combination thereof;
4. a lubricant such as magnesium stearate, calcium stearate or steorotes, talc, solid polyethylene glycols, sodium lauryl sulphate or any other ingredient of the similar nature alone or in a suitable combination thereof;
5. a glidant such as colloidal silicon dioxide or any other ingredient of the similar nature alone or in a suitable combination thereof;
6. a sweetening agent such as sucrose, saccharin or any other ingredient of the similar nature alone or in a suitable combination thereof;
7. a flavoring agent such as peppermint, methyl salicylate, orange flavor, vanilla flavor, or any other pharmaceutically acceptable flavor alone or in a suitable combination thereof;
8. wetting agents such as cetyl alcohol, glyceryl monostearate or any other pharmaceutically acceptable flavor alone or in a suitable combination thereof;
9. absorbents such as kaolin, bentonite clay or any other pharmaceutically acceptable flavor alone or in a suitable combination thereof;
10. solution retarding agents such as wax, paraffin or any other pharmaceutically acceptable flavor alone or in a suitable combination thereof.

The following examples are given by way of illustration and should not construe the scope of the invention.

Examples of Benzfurochromenes and Related Compounds

Example-1

3-Allyloxy-4-methyl-6a,11a-dihydro-6H-benzo[4,5]furo[3,2-c]chromene (S-007-1500)

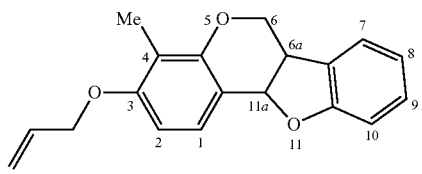 [SMILES: C=CCOc1ccc2c(c1C)OCC1c3ccccc3OC21]

Compound 4-methyl-6a,11a-dihydro-6H-benzo[4,5]furo[3,2-c]chromen-3-ol (100 mg, 0.34 mmol) was dissolved in DMF (5 ml) and NaH (8.1 mg, 0.34 mmol) was added to the solution at room temperature, followed by allyl bromide (0.06 ml, 0.68 mmol). The reaction mixture was stirred at room temperature to 6 hours and poured into iced water and neutralized with 10% HCl to get the white precipitate. Precipitate were washed with water and purified by silica gel column chromatography using hexane-chloroform as the eluent to give 3-isopropoxy-6a,11a-dihydro-6H-benzofuro[3,2-c]chromene (58 mg, 50%) as white solid.

white solid; mp 100-102° C.; $^1$H NMR (300 MHz, CDCl$_3$) δ 2.13 (s, 3H, CH$_3$), 3.53-3.73 (m, 2H, H-6β+H-6a), 4.32 (dd, J=4.4, 5.9 Hz, 1H, H-6α), 4.56 (d, J=5.0 Hz, 2H, CH$_2$), 5.27 (dd, J=1.4, 10.5 Hz, 1H, CH), 5.42 (dd, J=1.5, 17.3 Hz, 1H, CH), 5.53 (d, J=6.6 Hz, 1H, H-11a), 5.97-6.11 (m, 1H, CH), 6.62 (d, J=8.6 Hz, 1H, ArH), 6.84 (d, J=8.0 Hz, 1H, ArH), 6.89-6.94 (m, 1H, ArH), 7.13-7.19 (m, 1H, ArH), 7.27 (d, J=8.0 Hz, 1H, ArH), 7.33 (d, J=8.5 Hz, 1H, ArH); $^{13}$C NMR (75.5 MHz, CDCl$_3$) δ 7.10, 38.98, 65.26, 67.86, 77.10, 104.59, 108.84, 111.46, 113.47, 115.77, 119.49, 123.45, 126.07, 127.06, 127.84, 132.18, 153.06, 156.32, 158.14; MS (ESI) 295 (M$^+$+1); HRMS calcd. for C$_{19}$H$_{18}$O$_3$ 294.1256. found: 294.1241.

Example-2

1-(2-(6a,11a-Dihydro-6H-benzofuro[3,2-c]chromen-3-yloxy)ethyl)piperidine (S-008-0399)

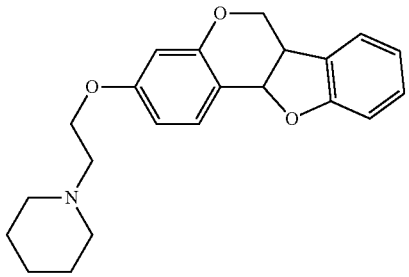 [SMILES: c1ccc2c(c1)OC1c3ccc(OCCN4CCCCC4)cc3OCC21]

Compound 6a,11a-dihydro-6H-benzo[4,5]furo[3,2-c]chromen-3-ol (100 mg, 0.42 mmol) was dissolved in DMF (5 ml) and NaH (10 mg, 0.42 mmol) was added to the solution at room temperature, followed by 1-(2-chloroethyl)piperidine hydrochloride (366 mg, 0.84 mmol). The reaction mixture was stirred at room temperature to 6 hours and poured into iced water and neutralized with 10% HCl to get the white precipitate. Precipitate were washed with water and purified by silica gel column chromatography using hexane-chloroform as the eluent to give 1-(2-(6a,11a-dihydro-6H-benzofuro[3,2-c]chromen-3-yloxy)ethyl)piperidine (102 mg, 70%) as white solid.

white solid; mp 202-204° C.; $^1$H NMR (300 MHz, CDCl$_3$) δ 1.44-1.72 (m, 6H, 3CH$_2$), 1.88-2.20 (m, 4H, 2CH$_2$), 3.28-3.40 (m, 2H, CH$_2$), 3.55-3.73 (m, 2H, H-6β+H-6a), 4.29 (dd, J=3.6, 9.7 Hz, 1H, H-6α), 4.46-4.58 (m, 2H, CH$_2$), 5.50 (d, J=6.3 Hz, 1H, H-11a), 6.47 (d, J=2.4 Hz, 1H, ArH), 6.63 (dd, J=2.5, 8.5 Hz, 1H, ArH), 6.81-6.95 (m, 2H, ArH), 7.10-7.28 (m, 2H, ArH), 7.46 (d, J=6.5 Hz, 1H, ArH); MS (ESI) 352 (M$^+$+1).

Example-3

4-Methyl-6a,11a-dihydro-6H-benzo[4,5]furo[3,2-c]chromen-3-ol (S-007-1499)

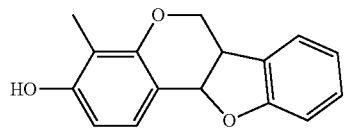

To a stirred solution of 7-hydroxy-3-(2-hydroxy-phenyl)-8-methyl-chromen-4-one (3 gm, 11.2 mmol) in absolute ethanol (30 ml) at 0° C. was added NaBH$_4$ (2.6 gm, 67.2 mmol). The reaction mixture was then stirred for 24 hours at room temperature. The reaction was stopped by adding ice-cooled water and the solution was neutralized with 10% HCl to get the white precipitate. The white precipitate was washed with water and the purified by silica gel column chromatography using hexane-chloroform as the eluent to give 4-methyl-6a,11a-dihydro-6H-benzo[4,5]furo[3,2-c]chromen-3-ol (1.56 gm, 55%) as white solid.

white solid; mp 160-162° C.; $^1$H NMR (300 MHz, CDCl$_3$) δ 2.12 (s, 3H, CH$_3$), 3.52-3.75 (m, 2H, H-6β+H-6a), 4.33 (dd, J=4.5, 5.8 Hz, 1H, H-6α), 4.87 (s, 1H, OH, D$_2$O exchange), 5.52 (d, J=6.6 Hz, 1H, H-11a), 6.55 (d, J=8.34 Hz, 1H, ArH), 6.81-6.94 (m, 2H, ArH), 7.13-7.23 (m, 1H, ArH), 7.24-7.30 (m, 2H, ArH); IR (KBr) 1479, 1552, 1599, 3383, 3407 cm$^{-1}$ (OH); MS (ESI) 255 (M$^+$+1).

Example-4

3-Isopropoxy-6a,11a-dihydro-6H-benzofuro[3,2-c]chromene (S-008-0398)

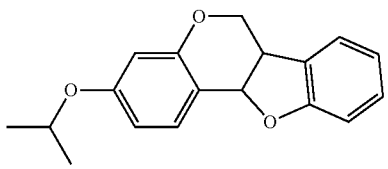 [SMILES: CC(C)Oc1ccc2c(c1)OCC1c3ccccc3OC21]

Compound 6a,11a-Dihydro-6H-benzo[4,5]furo[3,2-c]chromen-3-ol (100 mg, 0.42 mmol) was dissolved in DMF (5 ml) and NaH (10 mg, 0.42 mmol) was added to the solution at room temperature, followed by isopropyl iodide (149 mg, 0.84 mmol). The reaction mixture was stirred at room temperature to 6 hours and poured into iced water and neutralized with 10% HCl to get the white precipitate. Precipitate were washed with water and purified by silica gel column chromatography using hexane-chloroform as the eluent to give 3-isopropoxy-6a,11a-dihydro-6H-benzofuro[3,2-c]chromene (60 mg, 51%) as white solid.

white solid; mp 96-98° C.; $^1$H NMR (200 MHz, CDCl$_3$) δ 1.33 (d, J=6 Hz, 6H, 2CH$_3$) 3.51-3.75 (m, 2H, H-6β+H-6a), 4.28 (dd, J=3.3, 9.8 Hz, 1H, H-6α), 4.42-4.64 (m, 1H, CH), 5.50 (d, J=6.3 Hz, 1H, H-11a), 6.46 (d, J=2.4 Hz, 1H, ArH), 6.62 (dd, J=2.4, 8.4 Hz, 1H, ArH), 6.81-6.96 (m, 2H, ArH), 7.13-7.29 (m, 2H, ArH), 7.43 (d, J=8.5 Hz, 1H, ArH); $^{13}$C-NMR (75.5 MHz, CDCl$_3$) δ 22.00, 40.15, 66.36, 66.99, 77.78, 103.50, 110.21, 110.73, 112.00, 120.8, 124.72, 127.20, 129.19, 131.88, 156.55, 159.40; IR (KBr) 744, 784, 876, 928, 981, 1038, 1132, 1174, 1229, 1279, 1371, 1461, 1502, 1577, 1625, 2925, 2977, 3052 cm$^{-1}$; MS (ESI) 283 (M$^+$+1).

Example-5

3-(Allyloxy)-6a,11a-dihydro-6H-benzofuro[3,2-c]chromene (S-008-0625)

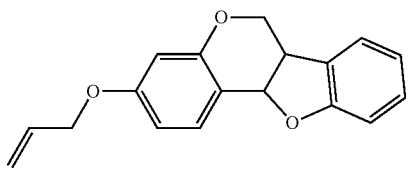 [SMILES: C=CCOc1ccc2c(c1)OCC1c3ccccc3OC21]

Compound 6a,11a-Dihydro-6H-benzo[4,5]furo[3,2-c]chromen-3-ol (100 mg, 0.42 mmol) was dissolved in DMF (5 ml) and NaH (10 mg, 0.42 mmol) was added to the solution at room temperature, followed by allyl bromide (0.07 ml, 0.84 mmol). The reaction mixture was stirred at room temperature to 6 hours and poured into iced water and neutralized with 10% HCl to get the white precipitate. Precipitate were washed with water and purified by silica gel column chromatography using hexane-chloroform as the eluent to give 3-(allyloxy)-6a,11a-dihydro-6H-benzofuro[3,2-c]chromene (58 mg, 50%) as white solid.

white solid; mp 72-74° C.; $^1$H NMR (300 MHz, CDCl$_3$) δ 3.56-3.72 (m, 2H, H-6β+H-6a), 4.27 (dd, J=4.3, 5.9 Hz, 1H, H-6α), 4.52 (d, J=5.2 Hz, 2H, CH$_2$), 5.28 (dd, J=1.2, 10.5 Hz, 1H, CH), 5.40 (dd, J=1.4, 17.3 Hz, 1H, CH), 5.49 (d, J=6.4 Hz, 1H, H-11a), 5.96-6.06 (m, 1H, CH), 6.48 (d, J=6.5 Hz, 1H, ArH), 6.66 (dd, J=2.4, 8.5 Hz, 1H, ArH), 6.81-6.94 (m, 2H, ArH), 7.13-7.22 (m, 1H, ArH), 7.22-7.28 (m, 1H, ArH), 7.43 (d, J=8.6 Hz, 1H, ArH); $^{13}$C NMR (75.5 MHz, CDCl$_3$) δ 40.12, 66.36, 68.87, 77.7, 102.56, 109.83, 110.22, 112.42, 117.89, 120.88, 124.74, 127.25, 129.23, 131.91, 132.95, 156.52, 159.35, 160.00; IR (KBr) 757, 803, 833, 869, 888, 907, 931, 995, 1033, 1086, 1111, 1178, 1230, 1266, 1304, 1337, 1385, 1432, 1461, 1478, 1504, 1585, 1619, 2898, 2925, 2989, 3016, 3050 cm$^{-1}$; MS (ESI) 280 (M$^+$+1).

Example-6

(4-Methyl-6a,11a-dihydro-6H-benzo[4,5]furo[3,2-e]chromen-3-yloxy)-acetonitrile (S-007-1501)

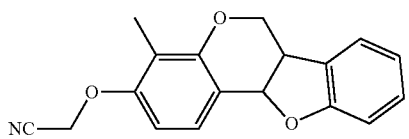 [SMILES: Cc1c(OCC#N)ccc2c1OCC1c3ccccc3OC21]

Compound 4-methyl-6a,11a-dihydro-6H-benzo[4,5]furo[3,2-c]chromen-3-ol (100 mg, 0.34 mmol) was dissolved in DMF (5 ml) and NaH (8.1 mg, 0.34 mmol) was added to the solution at room temperature, followed by 2-bromoacetonitrile (0.05 ml, 0.68 mmol). The reaction mixture was stirred at room temperature to 6 hours and poured into iced water and neutralized with 10% HCl to get the white precipitate. Precipitate were washed with water and purified by silica gel column chromatography using hexane-chloroform as the eluent to give 3-isopropoxy-6a,11a-dihydro-6H-benzofuro[3,2-c]chromene (63.5 mg, 55%) as white solid.

white solid; mp 130-132° C.; $^1$H NMR (300 MHz, CDCl$_3$) δ 2.12 (s, 3H, CH$_3$), 3.56-3.74 (m, 2H, H-6β+H-6a), 4.35 (dd, J=4.0, 6.0 Hz, 1H, H-6α), 4.79 (s, 2H, OH, CH$_2$), 5.53 (d, J=6.5 Hz, 1H, H-11a), 6.69 (d, J=8.6 Hz, 1H, ArH), 6.85 (d, J=8.0 Hz, 1H, ArH), 6.87-6.96 (m, 1H, ArH), 7.14-7.23 (m, 1H, ArH), 7.27 (d, J=8.0 Hz, 1H, ArH), 7.41 (d, J=8.6 Hz, 1H, ArH); $^{13}$C NMR (75.5 MHz, CDCl$_3$) δ 7.12, 38.89, 52.88, 65.29, 76.60, 104.54, 108.89, 113.90, 114.70, 119.67, 123.47, 125.73, 127.51, 127.97, 153.48, 154.22, 156.11, 158.01; IR (KBr) 753, 798, 825, 891, 934, 986, 1018, 1121, 1176, 1234, 1277, 1316, 1352, 1390, 1481, 1612 cm$^{-1}$, 2273 cm$^{-1}$ (CN); MS (ESI) 293, 269 (M$^+$, M$^+$+1-CN).

Example-7

6a,11a-Dihydro-6H-benzo[4,5]furo[3,2-c]chromen-3-ol (S-006-1709)

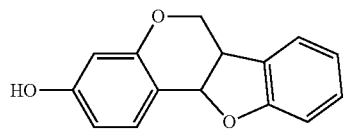 [SMILES: Oc1ccc2c(c1)OCC1c3ccccc3OC21]

To a stirred solution of 7-hydroxy-3-(2-hydroxy-phenyl)-chromen-4-one (3 gm, 11.8 mmol) in absolute ethanol (30 ml) at 0° C. was added NaBH$_4$ (2.7 gm, 70.8 mmol). The reaction mixture was then stirred for 24 hours at room temperature. The reaction was stopped by adding ice-cooled water and the solution was neutralized with 10% HCl to get the white precipitate. The white precipitate was washed with water and the purified by silica gel column chromatography using hexane-chloroform as the eluent to give 6a,11a-dihydro-6H-benzo[4,5]furo[3,2-c]chromen-3-ol (1.6 gm, 57%) as white solid.

white solid; mp 148-152° C.; $^1$H NMR (200 MHz, CDCl$_3$) δ 3.57-3.74 (m, 2H, H-6β+H-6a), 4.22-4.33 (m, 1H, H-6α), 5.19 (s, 1H, OH, D$_2$O exchange), 5.49 (d, J=6.2 Hz, 1H, H-11a), 6.42 (d, J=2.4 Hz, 1H, ArH), 6.56 (dd, J=2.4, 8.4 Hz, 1H, ArH), 6.81-6.96 (m, 2H, ArH), 7.17 (d, J=7.76 Hz, 1H, ArH), 7.22-7.30 (m, 1H, ArH), 7.41 (d, J=8.4 Hz, 1H, ArH); IR (KBr) 1017, 1082, 1122, 1170, 1222, 1259, 1289, 1351, 1381, 1476, 1516, 1597, 3396 cm$^{-1}$ (OH); MS (ESI) 241 (M$^+$+1).

Example-8

3-Hydroxy-6H-benzofuro[3,2-c]chromen-6-one (S-008-400)

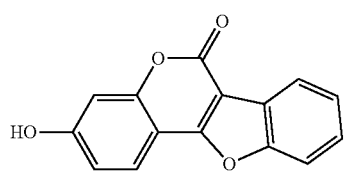 [SMILES: O=c1oc2cc(O)ccc2c2oc3ccccc3c12]

The compound 6a,11a-Dihydro-6H-benzo[4,5]furo[3,2-c]chromen-3-ol (100 mg, 0.42 mmol) was refluxed with DDQ (190.7 mg, 0.84 mmol) in toluene (10 ml) for 10 hours. The precipitated hydroquinone was filtered, and the solvent was removed from the filtrate. The residue was purified by passing through a silica gel column and eluting with chloroform-methanol.

White solid; mp 170-172° C.; $^1$H NMR (300 MHz, CDCl$_3$) δ 6.90-6.97 (m, 2H, ArH), 7.40-7.47 (m, 2H, ArH), 7.60-7.68 (m, 1H, ArH), 7.87 (d, J=8.2 Hz, 1H, ArH), 8.02-8.10 (m, 1H, ArH); IR (KBr) 746, 773, 807, 855, 951, 1000, 1122, 1264, 1309, 1372, 1440, 1610, 1730 (CO), 2927, 3085 cm$^{-1}$; MS (ESI) 252 (M$^+$+1).

New Isoflavones Precursors

Example-9

7,8-Dihydroxy-3-(2-methoxy-phenyl)-chromen-4-one (S-007-1352)

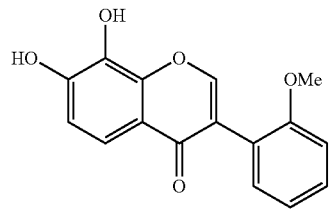 [SMILES: COc1ccccc1-c1coc2c(O)c(O)ccc2c1=O]

BF$_3$—OEt$_2$ complex (7 ml, 56 mmol) was gradually added to a solution of 2-(2-methoxy-phenyl)-1-(2,3,4-trihydroxy-phenyl)-ethanone (3.8 gm, 14 mmol) in DMF at 0° C. The resulting solution was stirred for 30 min. Mesityl chloride (1.5 ml, 42 mmol) was then gradually added to it at 50° C. The solution was then heated up to 110° C. for 5 hours. The mixture was then concentrated. The residue was treated with ice and the solid obtained was purified with silica gel column chromatography using hexane-chloroform as the eluent to give 7,8-dihydroxy-3-(2-methoxy-phenyl)-chromen-4-one (0.98 gm, 25%) as white solid.

white solid; mp 220-222° C.; $^1$H NMR (300 MHz, CDCl$_3$+DMSO) δ 3.10 (s, 3H, OCH$_3$), 6.94-7.05 (m, 3H, ArH), 7.25-7.38 (m, 2H, ArH), 7.55-7.65 (m, 1H, ArH), 7.98 (s, 1H, CH), 8.74 (s, 1H, OH), 9.54 (s, 1H, OH); $^{13}$C NMR (50 MHz, CDCl$_3$+DMSO) 560.85, 110.37, 119.53, 121.53, 123.21, 125.53, 126.46, 126.69, 134.77, 136.96, 138.08, 152.23, 154.99, 158.81, 162.73, 180.92; IR (KBr) 1629 cm$^{-1}$ (CO); MS (ESI) 285 (M$^+$+1).

Example-10

7,8-Dihydroxy-3-(2-hydroxy-phenyl)-chromen-4-one (S-007-1351)

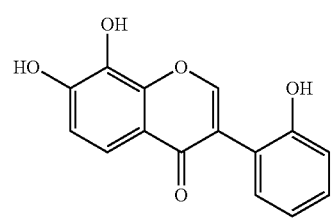 [SMILES: O=c1c(-c2ccccc2O)coc2c(O)c(O)ccc12]

To a stirred solution of 7,8-dihydroxy-3-(2-methoxyphenyl)-4H-chromen-4-one (2 gm, 7.1 mmol) in dry CH$_2$Cl$_2$ (50 ml) at −80° C. was added BBr$_3$ (1.4 ml in DCM, 14.2 mmol). The reaction mixture was then stirred for 1 hour at −80° C.

and 12 hours at room temperature. The reaction was then quenched with ice-cooled water. The reaction mixture was then extracted with $CH_2Cl_2$ and the organic layer was separated, washed with brine, dried over $Na_2SO_4$, and evaporated. The residue was purified by silica gel column chromatography using hexane-chloroform as the eluent to give 7,8-dihydroxy-3-(2-hydroxy-phenyl)-chromen-4-one (0.95 gm, 50%) as white solid.

white solid; mp 240-242° C.; $^1$H NMR (300 MHz, $CDCl_3$+ DMSO) δ 6.91-7.00 (m, 1H, ArH), 7.01-7.13 (m, 2H, ArH), 7.21 (d, J=7.6 Hz, 1H, ArH), 7.25-7.35 (m, 1H, ArH), 7.72 (d, J=7.6 Hz, 1H, ArH), 8.18 (s, 1H, CH), 9.17 (s, 1H, OH); IR (KBr) 1723 $cm^{-1}$ (CO); MS (ESI) 271 ($M^+$+1).

Example-11

6-Chloro-7-hydroxy-3-(2-methoxy-phenyl)-chromen-4-one (S-007-1355)

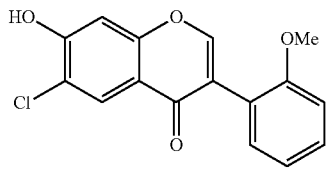

$BF_3$—$OEt_2$ complex (7 ml, 56 mmol) was gradually added to a solution of 1-(5-chloro-2,4-dihydroxy-phenyl)-2-(2-methoxy-phenyl)-ethanone (4.1 gm, 14 mmol) in DMF at 0° C. The resulting solution was stirred for 30 min. Mesityl chloride (1.5 ml, 42 mmol) was then gradually added to it at 50° C. The solution was then heated up to 110° C. for 5 hours. The mixture was then concentrated. The residue was treated with ice and the solid obtained was purified with silica gel column chromatography using hexane-chloroform as the eluent to give 6-chloro-7-hydroxy-3-(2-methoxy-phenyl)-chromen-4-one (2.5 gm, 60%) as white solid.

white solid; mp 228-230° C.; $^1$H NMR (300 MHz, $CDCl_3$+ DMSO) δ 3.79 (s, 3H, $OCH_3$), 6.95-7.09 (m, 3H, ArH), 7.24-7.40 (m, 2H, ArH), 7.91 (s, 1H, ArH), 8.13 (s, 1H, CH), 10.85 (s, 1H, OH); $^{13}$C NMR (75.5 MHz, $CDCl_3$+DMSO) δ 59.16, 107.43, 114.68, 121.50, 123.75, 123.90, 124.32, 125.70, 130.29, 133.23, 135.11, 157.33, 159.60, 160.96, 161.45, 178.50; IR (KBr) 1625 $cm^{-1}$ (CO); MS (ESI) 303 ($M^+$+1).

Example-12

6-Chloro-7-hydroxy-3-(2-hydroxy-phenyl)-chromen-4-one (S-007-1354)

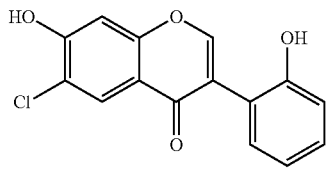 [SMILES: O=c1c(-c2ccccc2O)coc2cc(O)c(Cl)cc12]

To a stirred solution of 6-chloro-7-hydroxy-3-(2-methoxyphenyl)-4H-chromen-4-one (2.5 gm, 8.3 mmol) in dry $CH_2Cl_2$ (25 ml) at −80° C. was added $BBr_3$ (1.6 ml in DCM, 16.6 mmol). The reaction mixture was then stirred for 1 hour at −80° C. and 12 hours at room temperature. The reaction was then quenched with ice-cooled water. The reaction mixture was then extracted with $CH_2Cl_2$ and the organic layer was separated, washed with brine, dried over $Na_2SO_4$, and evaporated. The residue was purified by silica gel column chromatography using hexane-chloroform as the eluent to give 6-chloro-7-hydroxy-3-(2-hydroxy-phenyl)-chromen-4-one (1.4 gm, 60%) as white solid.

white solid; mp>250° C.; $^1$H NMR (300 MHz, $CDCl_3$+ DMSO) δ 6.95-7.04 (m, 3H, ArH), 7.20-7.32 (m, 2H, ArH), 8.11 (s, 1H, ArH), 8.20 (s, 1H, CH), 9.05 (s, 1H, OH); IR (KBr) 1625 $cm^{-1}$ (CO); MS (ESI) 289 ($M^+$+1).

Example-13

7-Hydroxy-3-(2-hydroxy-phenyl)-8-methyl-chromen-4-one (S-007-1498)

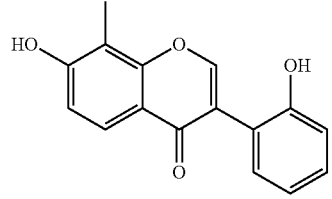 [SMILES: Cc1c(O)ccc2c(=O)c(-c3ccccc3O)coc12]

To a stirred solution of 7-hydroxy-3-(2-methoxyphenyl)-8-methyl-4H-chromen-4-one (5 gm, 17.7 mmol) in dry $CH_2Cl_2$ (50 ml) at −80° C. was added $BBr_3$ (3.4 ml in DCM, 35.4 mmol). The reaction mixture was then stirred for 1 hour at −80° C. and 12 hours at room temperature. The reaction mixture was then quenched with ice-cooled water. The reaction mixture was then extracted with $CH_2Cl_2$ and the organic layer was separated, washed with brine, dried over $Na_2SO_4$, and evaporated. The residue was purified by silica gel column chromatography using hexane-chloroform as the eluent to give 7-hydroxy-3-(2-hydroxy-phenyl)-8-methyl-chromen-4-one (3.5 gm, 72%) as white solid.

white solid; mp 196-198° C.; $^1$H NMR (300 MHz, $CDCl_3$+ DMSO) δ 2.34 (s, 3H, $CH_3$), 6.90-7.06 (m, 3H, ArH), 7.22-7.32 (m, 2H, ArH), 7.95-8.04 (m, 1H, ArH), 8.18 (s, 1H, CH), 10.18 (s, 1H, OH, $D_2O$ exchange); IR (KBr) 1625 $cm^{-1}$ (CO); MS (ESI) 269 ($M^+$+1).

Known Isoflavones'Precursors

Example-14

7-Hydroxy-3-(2-methoxy-phenyl)-chromen-4-one (S-006-1710)

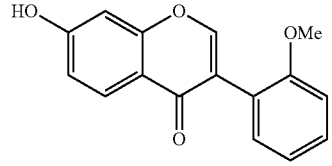 [SMILES: COc1ccccc1-c1coc2cc(O)ccc2c1=O]

$BF_3$—$OEt_2$ complex (14 ml, 112 mmol) was gradually added to a solution of 1-(2,4-dihydroxy-phenyl)-2-(2-methoxy-phenyl)-ethanone (7.2 gm, 28 mmol) in DMF at 0° C.

The resulting solution was stirred for 30 min. Mesityl chloride (6.5 ml, 84 mmol) was then gradually added to it at 50° C. The solution was then heated up to 110° C. for 5 hours. The mixture was then concentrated. The residue was treated with ice and the solid obtained was purified with silica gel column chromatography using hexane-chloroform as the eluent to give 7-hydroxy-3-(2-methoxy-phenyl)-chromen-4-one (5.6 gm, 75%) as white solid.

white solid; mp 222-224° C.; $^1$H NMR (200 MHz, CDCl$_3$+ CD$_3$OD) δ3.80 (s, 3H, OCH$_3$), 6.85-7.07 (m, 4H, ArH), 7.23-7.41 (m, 2H, ArH), 7.96 (s, 1H, CH), 8.08 (d, J=8.8 Hz, 1H, ArH); IR (KBr) 1628 cm$^{-1}$ (CO); MS (ESI) 269 (M$^+$+1).

Example-15

7-Hydroxy-3-(2-hydroxy-phenyl)-chromen-4-one (S-006-1711)

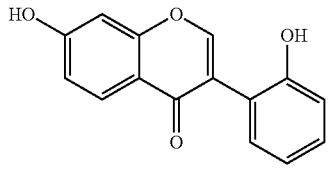 [SMILES: O=c1c(-c2ccccc2O)coc2cc(O)ccc12]

To a stirred solution of 7-hydroxy-3-(2-methoxy-phenyl)-chromen-4-one (5 gm, 18.7 mmol) in dry CH$_2$Cl$_2$ (50 ml) at −80° C. was added BBr$_3$ (3.6 ml in DCM, 37.4 mmol). The reaction mixture was then stirred for 1 hour at −80° C. and 12 hours at room temperature. The reaction was then quenched with ice-cooled water. The reaction mixture was then extracted with CH$_2$Cl$_2$ and the organic layer was separated, washed with brine, dried over Na$_2$SO$_4$, and evaporated. The residue was purified by silica gel column chromatography using hexane-chloroform as the eluent to give 7-hydroxy-3-(2-hydroxy-phenyl)-chromen-4-one (3.8 gm, 80%) as white solid.

white solid; mp 196-198° C.; $^1$H NMR (200 MHz, CDCl$_3$+ CD$_3$OD) δ 6.89-7.05 (m, 4H, ArH), 7.20-7.36 (m, 2H, ArH), 8.12 (s, 1H, CH), 8.15 (d, J=9.04 Hz, 1H, ArH); IR (KBr) 1621 cm$^{-1}$ (CO); MS (ESI) 255 (M$^+$+1).

Example-16

3-(2,4-Dimethoxy-phenyl)-7-hydroxy-chromen-4-one (S-006-1713)

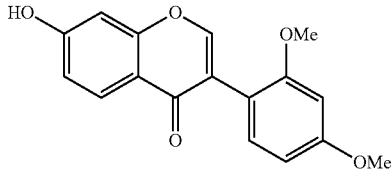 [SMILES: COc1ccc(-c2coc3cc(O)ccc3c2=O)c(OC)c1]

BF$_3$—OEt$_2$ complex (14 ml, 112 mmol) was gradually added to a solution of 1-(2,4-dihydroxy-phenyl)-2-(2,4-dimethoxy-phenyl)-ethanone (8.1 gm, 28 mmol) in DMF at 0° C. The resulting solution was stirred for 30 min. Mesityl chloride (6.5 ml, 84 mmol) was then gradually added to it at 50° C. The solution was then heated up to 110° C. for 5 hours. The mixture was then concentrated. The residue was treated with ice and the solid obtained was purified with silica gel column chromatography using hexane-chloroform as the eluent to give 3-(2,4-dimethoxy-phenyl)-7-hydroxy-chromen-4-one (5.9 gm, 70%) as white solid.

white solid; mp 238-240° C.; $^1$H NMR (200 MHz, CDCl$_3$+ CD$_3$OD) δ3.78 (s, 3H, OCH$_3$), 3.85 (s, 3H, OCH$_3$), 6.53-6.59 (m, 2H, ArH), 6.83-6.98 (m, 2H, ArH), 7.20 (d, J=8.9 Hz, 1H, ArH) 7.92 (s, 1H, CH), 8.08 (d, J=8.8 Hz, 1H, ArH); IR (KBr) 1621 cm$^{-1}$ (CO); MS (ESI) 299 (M$^+$+1).

Example-17

7-Hydroxy-3-(2-hydroxy-4-methoxy-phenyl)-chromen-4-one (S-006-1714)

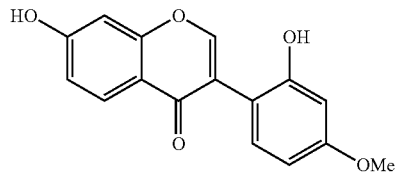 [SMILES: COc1ccc(-c2coc3cc(O)ccc3c2=O)c(O)c1]

Compound 3-(2,4-dimethoxy-phenyl)-7-hydroxy-chromen-4-one (2 gm, 6.7 mmol) was dissolved in CH$_3$CN (25 ml) and AlCl$_3$ (2.6 gm, 20 mmol) was added to the solution at 0° C. The reaction was then refluxed for 10 hours. The mixture was cooled and then poured ice-cooled water. The precipitated solid were filtered, washed with water and purified by silica gel column chromatography using chloroform-methanol as the eluent to give 7-hydroxy-3-(2-hydroxy-4-methoxy-phenyl)-chromen-4-one (0.95 gm, 50%) as white solid.

white solid; mp 210-212° C.; $^1$H NMR (300 MHz, CDCl$_3$+ CD$_3$OD) δ3.86 (s, 3H, OCH$_3$), 6.51-6.65 (m, 2H, ArH), 6.90 (d, J=1.9 Hz, 1H, ArH), 7.03 (dd, J=2.2, 10.28 Hz, 1H, ArH), 7.13 (d, J=8.4 Hz, 1H, ArH), 8.07 (s, 1H, CH), 8.15 (d, J=8.9 Hz, 1H, ArH); IR (KBr) 1619 cm$^{-1}$ (CO); MS (ESI) 285 (M$^+$+1).

Biological Evaluation

Pure compounds of the present invention were evaluated for the use of enhancement of osteogenesis bone formation, prevention or treatment of symptoms of estrogen deficiency or deprivation including estrogen deficient or deprivation state in mammals, in particular osteoporosis, bone formation, bone loss in humans and in other animals. Detailed procedures for the evaluation of isolated compounds of the present invention are described subsequently. The pharmacokinetic evaluations of the compound S006-1709 of the present invention were carried out in experimental animals and the detailed procedures are described. The activity testing illustrated in the following examples should, however, not be construed to limit the scope of invention.

Test Procedure for the Determination of Osteogenic or Bone Forming Activity

Test solutions of the test compounds of the present invention are prepared in appropriate solvents in concentration range of 10$^{-14}$M to 10$^{-6}$ M. 2 μl of each concentration are used for evaluation of bone forming in vitro. In control experiments, equal quantity of appropriate solvent is used in lieu of the test agent.

Osteoblast Cell Culture

Osteoblasts arise from pluripotent mesenchymal stem cells. One of the richest sources of pre-osteoblasts is the calvaria of newborn rat or mouse. Osteoblasts are also present in the bone marrow. During the course of culture, pre-osteoblasts undergo three Characteristic stages of osteoblasts with the expression of stage specific genes. These are:
Proliferation & differentiation: Days 1-12
Genes—Alkaline phosphatase, Collagen-I, Osterix, cbfa1
Extra-cellular matrix maturation: Days 12-18
Genes—Osteocalcin, Osteopontin, Fibronectin
Mineralization: Days 14-35
Feature—Calcification (nodule formation)

Neonatal rat calvarial cell cultures are prepared as described previously (Endocrinology 145:3451) using slight modification. Briefly, for primary osteoblast cell cultures, frontal and parietal bones from Sprague-Dawley rat neonates (1-3 day old) are digested in 0.1% collagenase/0.1% dispase in α-MEM to obtain 5 sequential digests. The second through fifth digests are combined and grown to confluence at 37° C. and 5% $CO_2$ in air in α-MEM, supplemented with 10% fetal bovine serum (FBS), 2 mM glutamine, 100 U/ml penicillin-streptomycin, Non-essential amino acid solution and sodium pyruvate.

Pure compounds were tested on osteoblasts and osteoclasts.

MTT Cell Proliferation Assay

Principle

MTT [3-(4,5-dimethylthiazol-2-yl)-2,5-diphenyltetrazolium bromide] assay, first described by Mosmann in 1983, is based on the ability of a mitochondrial dehydrogenase enzyme from viable cells to cleave the tetrazolium rings of the pale yellow MTT and form a dark blue formazan crystals which is largely impermeable to cell membranes, thus resulting in its accumulation within healthy cells. Solubilisation of the cells by the addition of a detergent results in the liberation of the crystals which are solubilized. The number of surviving cells is directly proportional to the level of the formazan product created. The color can then be quantified using a simple colorimetric assay. The results can be read on a multiwell scanning spectrophotometer (Mosmann T. Rapid colorimetric assay for cellular growth and survival: application to proliferation and cytotoxicity assays. J Immunol Methods. 1983 Dec. 16; 65(1-2):55-63).

Material and Method

Calvarial osteoblast cells plated at a density of $2.0 \times 10^3$ cells/200 ul in 96 wells plates. Cells were grown to 60% confluency and then treated with following compounds S006-1709, S006-1710, 5006-1711, S006-1713 and; S006-1714 at concentrations ranging from $10^{-10}$ M to $10^{-6}$ M for 24 hrs. After treatment media was removed and 10 mM MTT was added solution in phenol red free DMEM media. After an incubation of 4 hrs the MTT solution was removed. Blue colored crystals were formed which were dissolved in DMSO and absorbance was read on ELISA plate reader at 570 nm wavelength.

Result—

Compound S006-1709 had no effect on osteoblast proliferation (FIG. 1a).

Figure 3A:
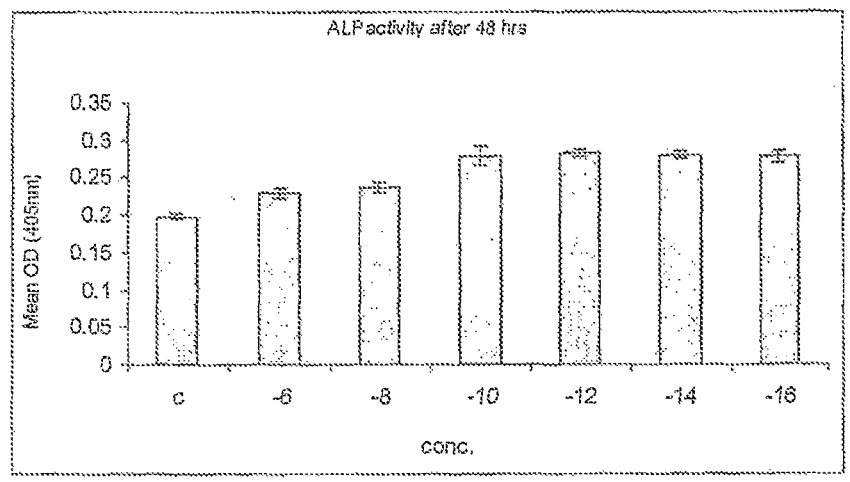
FIG. 3a illustrates the effect of Compound S006-1709 on osteoblast ALP activity at concentrations ranging from $10^{-16}$M to $10^{-6}$M studied.
Figure 5:
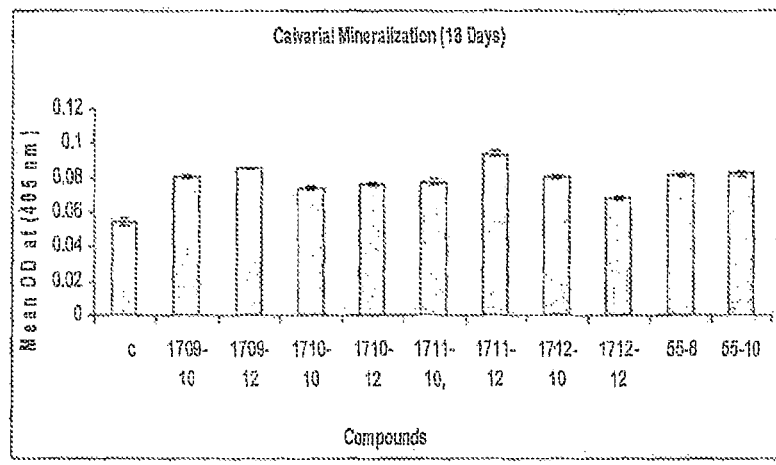
FIG. 5 illustrates the effect of S006-1709 to S006-1711 on mineralization of calvarial osteoblasts.

Alkaline Phosphatase Activity for Osteoblast Differentiation 70 to 80% confluent Calvarial osteoblasts were treated with µM S006-1709 for 48 h in the presence of ascorbate and glycerophosphate. At the end of incubation period, total ALP activity was measured with a method using p-nitrophenylphosphate (PNPP) as substrate. The reaction mixture contained diethanolamine buffer (1 mol/L, pH 9.8), 0.5 mmol/L $MgCl_2.6H_2O$, and 10 mmol/L PNPP. ALP activity was measured by taking OD of the amount of colored product formed by the dephosphorylation of PNPP at 405 nm. Result revealed that compared with vehicle control, there was significant increase in the osteoblast ALP activity by S006-1709 treatment at concentrations ranging from $10^{-16}$M to $10^{-6}$M studied (FIG. 3a). In addition, the effect of S006-1709 on mineralization of calvarial osteoblasts was studied. Data revealed significant increase in the mineralization of nascent calcium deposition by S006-1709 over control by Alizarin red extraction at $10^{-12}$ M and $10^{-10}$ M (FIG. 5).

Recent reports show that the calvarial osteoblasts respond differently from bone marrow osteoblasts in response to various growth factors. Clearly, S006-1709 is acting as a growth- and function-promoting agent in calvarial osteoblasts. In post-menopausal and other aging-associated bone loss, the trabecular bones with marrow are affected. Osteoblasts in the marrow fail to form bone at the rate in which bone is lost. Therefore, enhancing bone forming ability of the osteoblast is the most preferred therapeutic mode of bone loss disorders.

Figure 6:
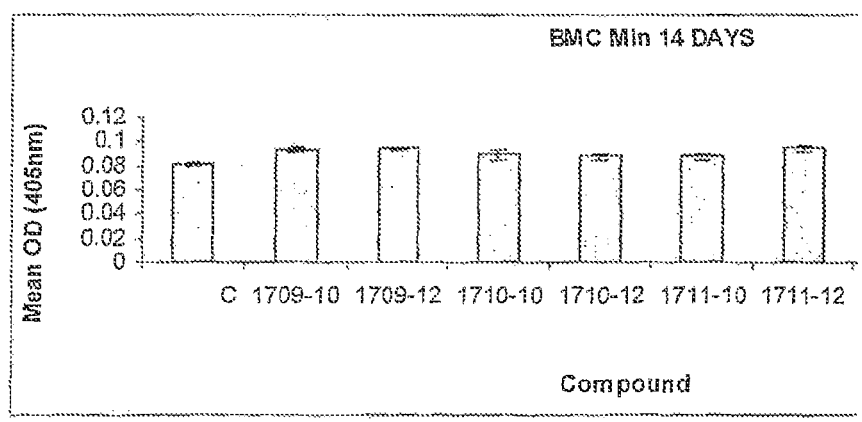
FIG. 6 illustrates the effect of S006-1709 to S006-1711 on mineralization of bone marrow osteoblasts.

In addition, the effect of S006-1709 on mineralization of bone marrow osteoblasts was also studied. Data revealed significant increase in the mineralization of nascent calcium deposition by S006-1709 over control by Alizarin red extraction at $10^{-12}$M and $10^{-10}$ M in 18 d bone marrow culture (FIG. 6).

S006-1710—

Figure 1B:
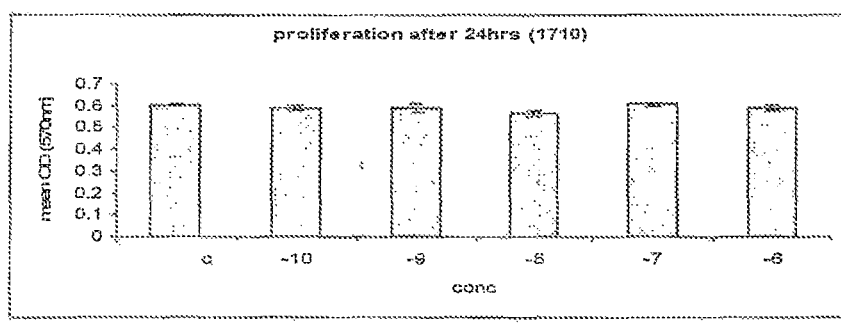
FIG. 1b represents the effect of Compound S006-1710 on osteoblast proliferation.

Using the similar study design as in S006-1709, we observed no osteoblast proliferating action of S006-1710 (FIG. 1b).

Figure 3B:
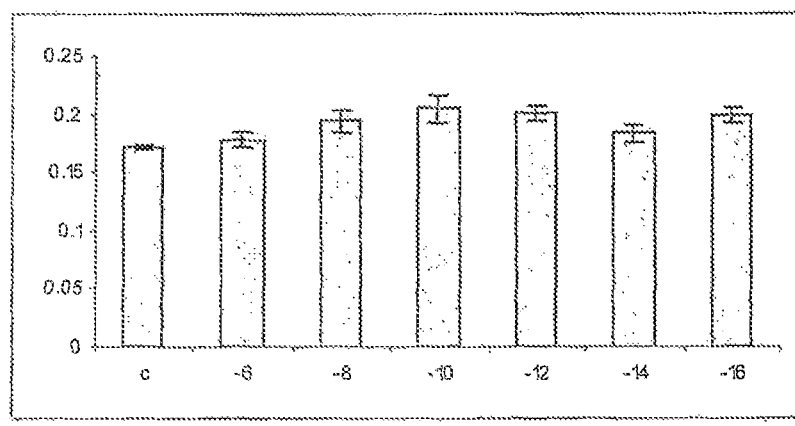
FIG. 3b illustrates the effect of S006-1710 in osteoblast differentiation in both calvarial and bone marrow osteoblasts.

We then studied its effect in osteoblast differentiation in both calvarial and bone marrow osteoblasts. Confluent calvarial osteoblasts (70 to 80%) were treated with S006-1710 for 48 h in the presence of ascorbate and glycerophosphate at concentrations ranging from $10^{-16}$M to $10^{-6}$M. At the end of incubation period, total ALP activity was measured with the same method used previously using p-nitrophenylphosphate (PNPP) as substrate. Result revealed that compared with vehicle control; there was significant increase in the osteoblast ALP activity by S006-1710 treatment at all concentrations studied (FIG. 3b).

S006-1710 was found to stimulate mineralization of calvarial and bone marrow osteoblasts at $10^{-12}$ M and $10^{-10}$ M concentrations as assessed by Alizarin red staining which is a measure of the amount of nascent calcium deposited. The effect was found to be similar to that of S006-1709 (FIG. 5).

In addition, the effect of S006-1710 on mineralization of bone marrow osteoblasts was also studied. Data revealed significant increase in the mineralization of nascent calcium deposition by S006-1710 over control by Alizarin red extraction at $10^{-12}$M and $10^{-10}$ M in 18 d bone marrow culture (FIG. 6).

S006-1711—

Figure 1C:
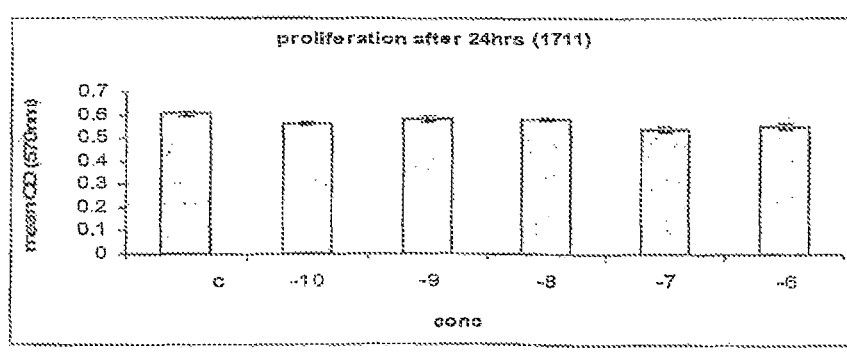
FIG. 1c illustrates the effect of Compound S006-1711 on osteoblast proliferation
Figure 3C:
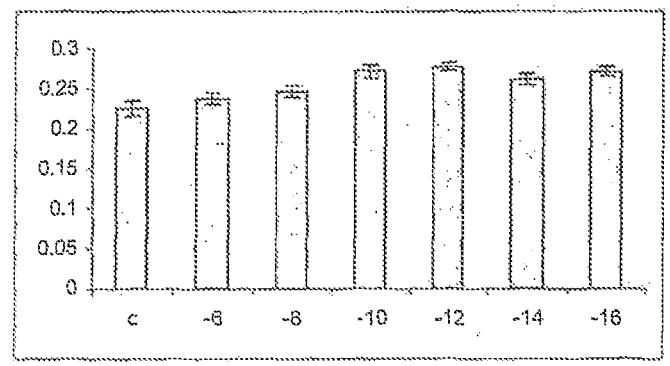
FIG. 3c illustrates the ALP activity of S006-1711 in calvarial and bone marrow derived osteoblasts.

S006-1711 did not have any effect on osteoblast proliferation (FIG. 1c) but stimulated ALP activity in calvarial and bone marrow derived osteoblasts from $10^{-16}$M to $10^{-6}$M concentrations (FIG. 3c). S006-1711 also stimulated mineralization of calvarial and bone marrow osteoblasts at $10^{-12}$ M and $10^{-10}$ M concentrations (FIG. 5 and FIG. 6).

S006-1713—

Figure 2A:
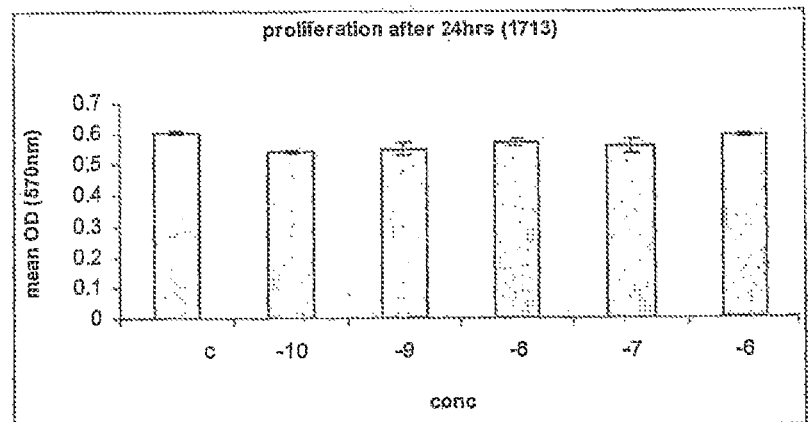
FIG. 2a illustrates the effect of Compound S006-1713 on osteoblast proliferation.
Figure 4A:
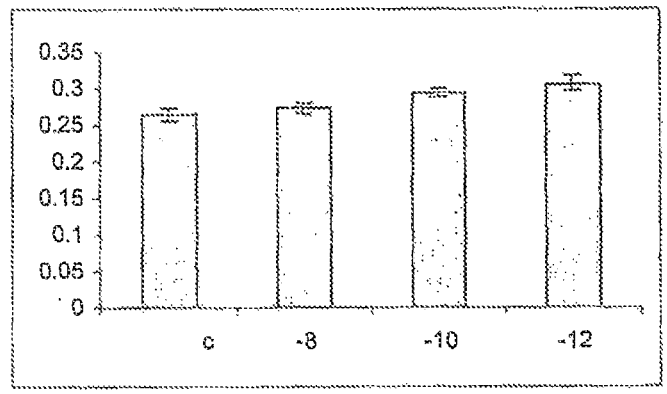
FIG. 4a illustrates the ALP activity of S006-1713.

S006-1713 did not have any effect on osteoblast proliferation (FIG. 2a) and stimulation of ALP activity was also found to be non-significant (FIG. 4a).

S006-1714—

Figure 2B:
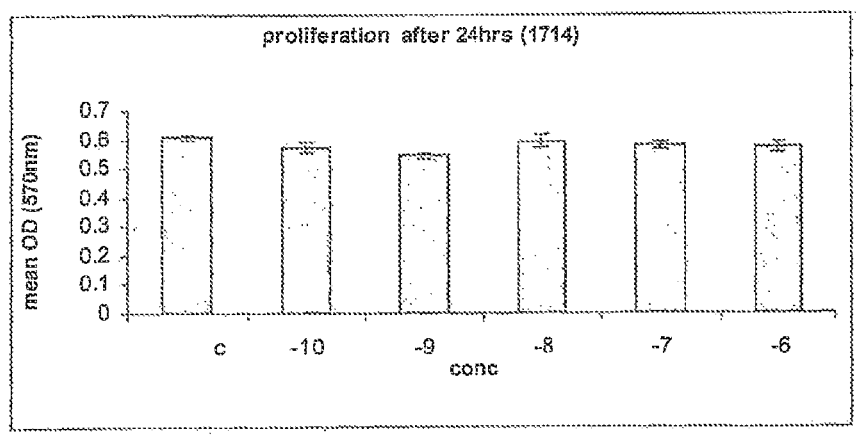
FIG. 2b illustrates the effect of Compound S006-1714 on osteoblast proliferation.
Figure 4B:
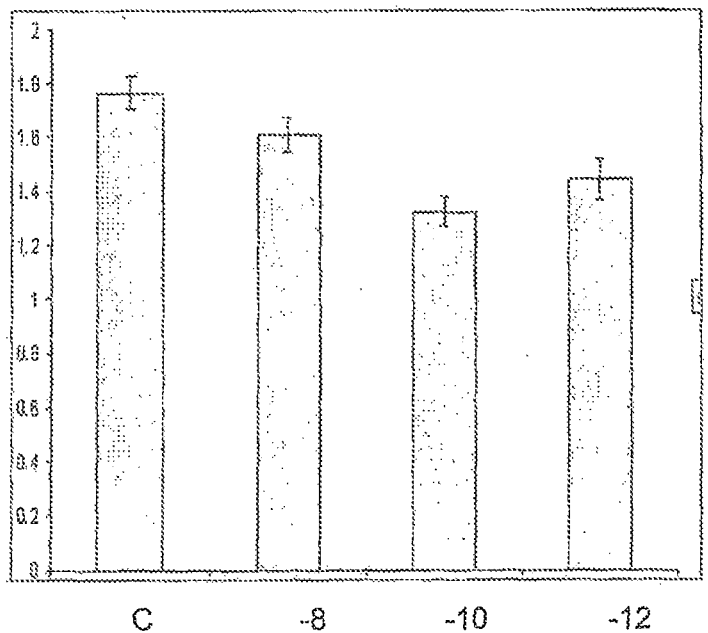
FIG. 4b illustrates the ALP activity of S006-1714

S006-1714 did not have any effect on osteoblast proliferation (FIG. 2b) and stimulation of ALP activity was also found to be non-significant (FIG. 4b).

Alkaline Phosphatase Activity for Osteoblast Differentiation
S007-1351

Figure 7:
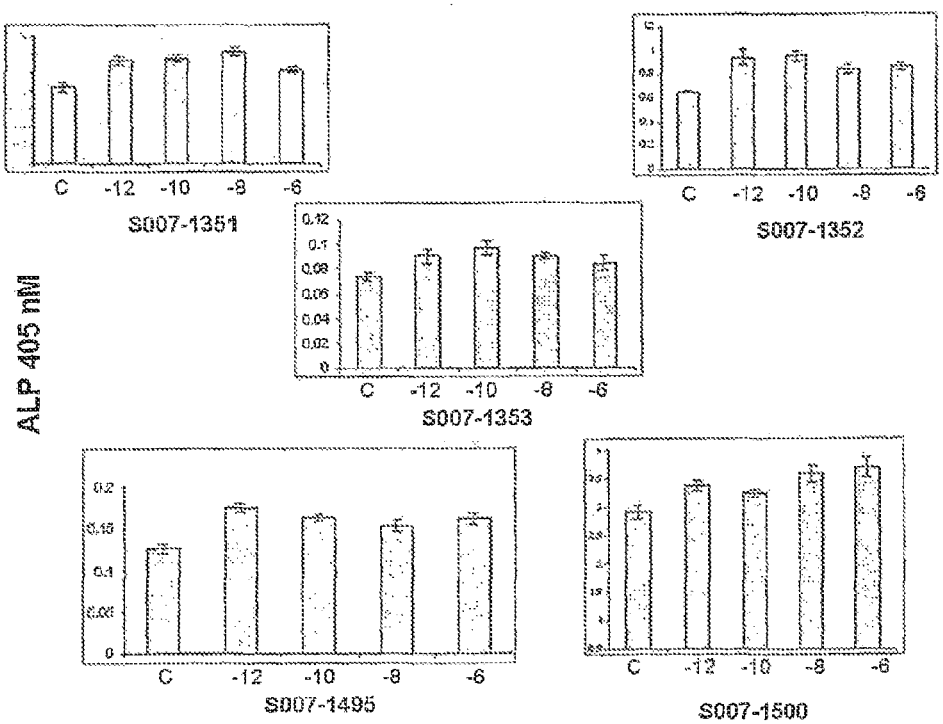
FIG. 7 illustrates the osteoblast ALP activity by S007-1351, S007-1352, S007-1353, S007-1495, S007-1500 at concentrations ranging from $10^{-12}$M to $10^{-6}$M studied.

70 to 80% confluent Calvarial osteoblasts were treated with S007-1351 for 48 h in the presence of ascorbate and glycerophosphate. At the end of incubation period, total ALP activity was measured with a method using p-nitrophenylphosphate (PNPP) as substrate. The reaction mixture contained diethanolamine buffer (1 mol/L, pH 9.8), 0.5 mmol/L $MgCl_2.6H_2O$, and 10 mmol/L PNPP. ALP activity was measured by taking OD of the amount of colored product formed by the dephosphorylation of PNPP at 405 nm. Result revealed that compared with vehicle control, there was significant increase in the osteoblast ALP activity by S007-1351 treatment at concentrations ranging from $10^{-12}$M to $10^{-6}$M studied (FIG. 7).
S006-1352

70 to 80% confluent calvarial osteoblasts were treated with S007-1352 for 48 h in the presence of ascorbate and glycerophosphate at concentrations ranging from $10^{-12}$M to $10^{-6}$ M. At the end of incubation period, total ALP activity was measured with the same method used previously using p-nitrophenylphosphate (PNPP) as substrate. Result revealed that compared with vehicle control; there was significant increase in the osteoblast ALP activity by S007-1352 treatment at all concentrations studied (FIG. 7).
S007-1353

S007-1353 stimulated ALP activity in calvarial derived osteoblasts from $10^{-12}$M to $10^{-6}$M concentrations (FIG. 7).
S007-1495—

S007-1495 stimulated ALP activity in calvarial derived osteoblasts from $10^{-12}$M to $10^{-6}$M concentrations (FIG. 7).
S007-1500—

S007-1500 stimulated ALP activity in calvarial derived osteoblasts from $10^{-12}$M to $10^{-6}$M concentrations (FIG. 7).
S007-1354, 5007-1355, 5007-1496, 5007-1497, 5007-1498, 5007-1499 and 5007-1501—

The stimulation of ALP activity with these compounds was found to be non-significant.
Anti-Adipogenic Effect of Various Synthesized Compounds
Principle:

This experiment was aimed to identify the synthetic compounds which could inhibit adipogenesis as the increase in adipogenesis has been shown to promote bone loss in vivo. The best characterized model of adipogenesis in vitro is the 3T3-L1 cell line, a substrain of Swiss 3T3 mouse cell line. 3T3-L1 cells propagated under normal conditions have a fibroblastic phenotype. However, when treated with a combination of dexamethasone, isobutylmethylxanthine (IBMX or MIX) and insulin, 3T3-L1 cells adopt a rounded phenotype and within 5 days begin to accumulate lipids intracellularly in the form of lipid droplets.
Method:
The Process of Adipogenesis (In Vitro)

3T3-L1 cells were plated in 48-well plates 40,000 cells/well. The cells were incubated in DMEM containing fetal calf serum for 2 days until the cells become confluent. The cells were then incubated with Adipogenesis initiation media which contains DMEM with 10% FCS, IBMX and dexamethasone for 48 hrs at 37° C., 5% $CO_2$. After two days the media was replaced with Adipogenesis Progression media which contains DMEM/10% FCS and insulin for 48 hrs at 37° C., 5% $CO_2$, Media was again changed gently to Adipogenesis maintenance media for 48 hrs at 37° C., 5% $CO_2$. At the end of eight days of experiment the cells were fixed and then stained with Oil Red O which stains lipid droplets. The dye was extracted and extracted dye was transferred to a 96-well plate and absorbance of extracted Oil Red O was measured in a plate reader at 490 nm.

Figure 8A:
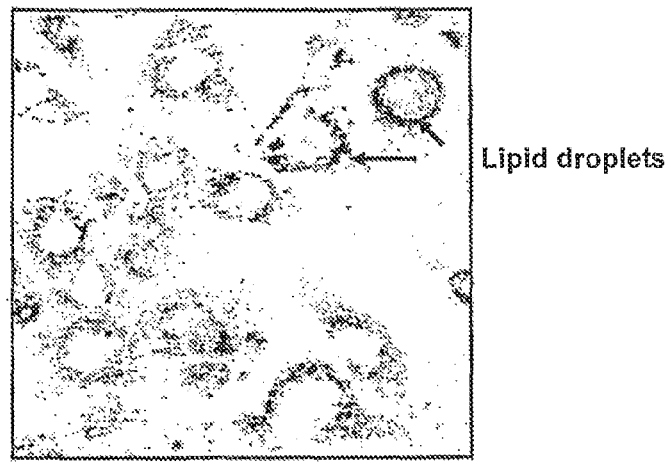
FIG. 8a depicts the adipocytes formed at the end of the 8 day experiment.
Figure 8B:
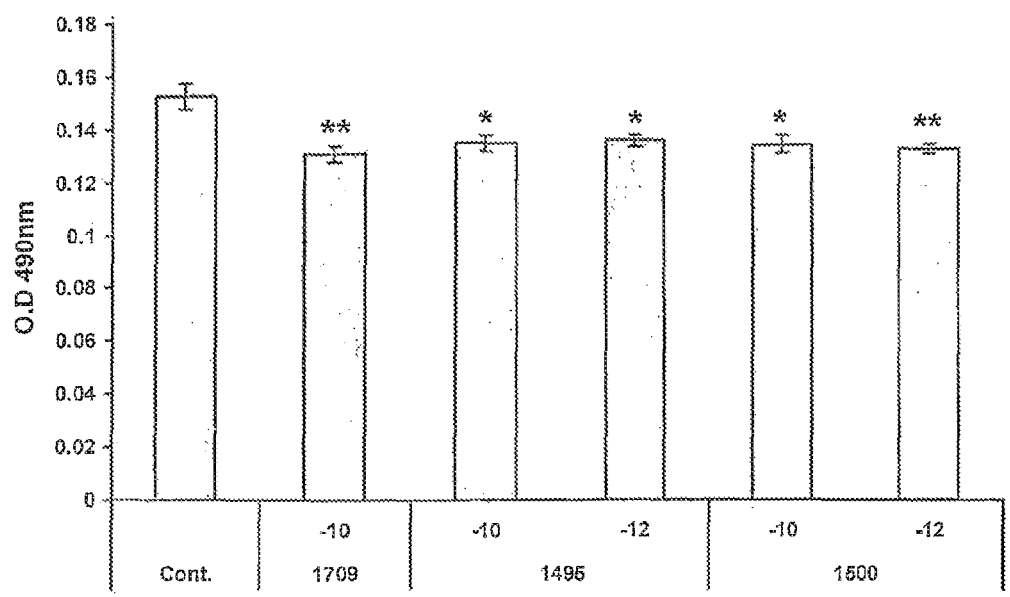
FIG. 8b represents the effect of compounds, S006-1709, S007-1495 and S007-1500 on adipogenesis at different concentrations
Figure 9:
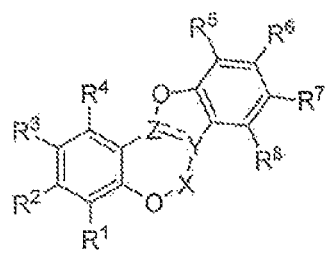
FIG. 9 depicts General Formula I, Template I and Template II.
Figure 9:
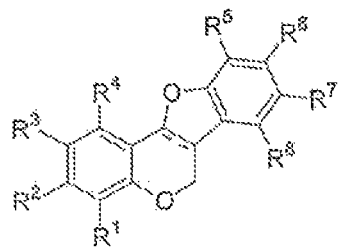
Figure 9:
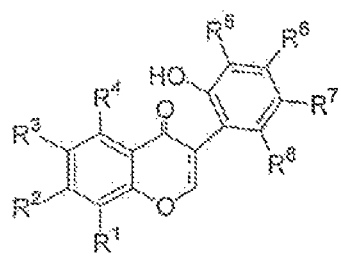
Figure 10:
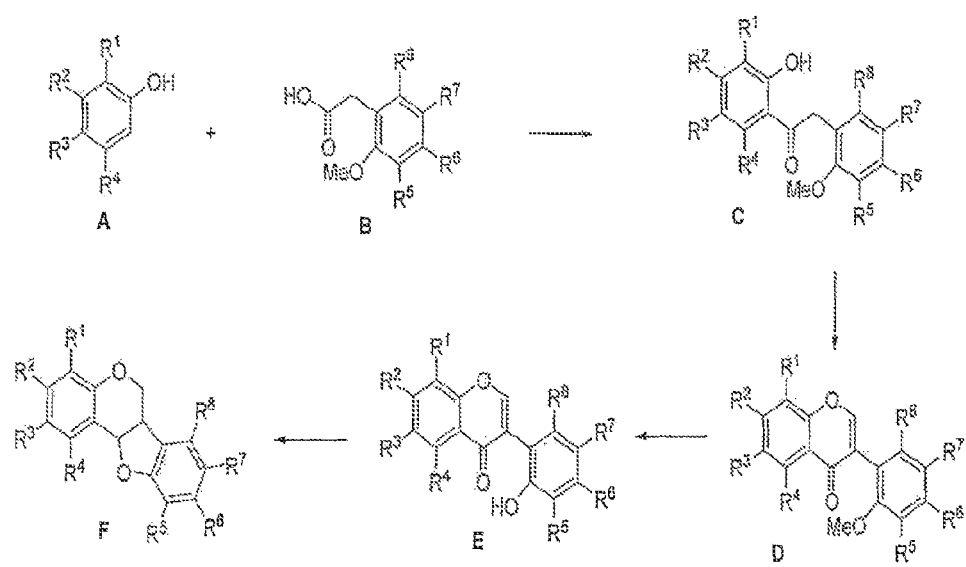
FIG. 10 depicts Scheme I.

Result:

Compounds S006-1709, S007-1351-53, S007-1495 and S007-1500 were tested in vitro in 3T3L1 cell line at two concentrations $10^{-10}$ M and $10^{-12}$M. FIG. 8A depicts the adipocytes formed at the end of the 8 day experiment. The fixed cells were stained with Oil Red O. The dye was then extracted and quantified. Out of all the compounds, S006-1709, S007-1495 and S007-1500 significantly inhibited adipogenesis at different concentrations (FIG. 8B). Compound S007-1353 inhibited adipogenesis at $10^{-10}$M but was not found to be statistically significant. The other compounds S007-1351 (both concentrations), S007-1352 (both concentrations) and S007-1353 at $10^{-12}$M concentration were found to be inducers of adipogenesis instead of being anti-adipogenic.
Estrogenicity and Anti-Estrogenicity Given the cancer promoting role of estrogen in post-menopausal women, a major drawback that has compelled discontinuation of estrogen therapy in these women, we tested the active pure compounds for their potential estrogenic property.

21 day old immature female rats (25-30 grams) were ovariectomized and given 7 days post-operative rest. Thereafter they were treated orally with the test agent (10 mg/Kg body weight) or with vehicle or Ethynyl estradiol, the reference standard for three consecutive days. For anti-estrogenicity, other than the test chemical, ethynyl estradiol (0.01 mg/kg) was given at 15 minutes interval before the test chemical. Autopsy was done 24 h after last treatment and uterine fresh weight was taken.

Compound S006-1709 was non-estrogenic while S006-1710 and S006-1711 were found to be estrogenic (Table 1). Compound S006-1709 was anti-estrogenic while S006-1710 and S006-1711 were not found to be anti-estrogenic (Table 1).

TABLE 1

| Treatment | Dose mg/Kg | Estrogenic Activity | Anti-Estrogenic Activity |
|---|---|---|---|
| Vehicle | | 16.46 | |
| Ethnyl Estradiol | 0.01 | 98.3 | |
| S006-1709 | 10 | 15.8 | 96.86 |
| | | — | −1.5% |
| S006-1710 | 10 | 89.96 | 79.9 |
| | | 446% | 19% |
| S006-1711 | 10 | 48.13 | 85.16 |
| | | 192% | 13% |

In Vivo Efficacy of S-006-1709 and S007-1500

Since S006-1709 and S007-1500 were found to exert stimulatory actions on all stages of osteoblast function, i.e. proliferation, differentiation and mineralization, and also was devoid of any estrogenicity, we evaluated S006-1709 (Table 2) and S007-1500 (Table 3) for in vivo efficacy.

Immature 21 d old female SD rat model was chosen, animals were randomized into four groups and treated with a daily dose of test agent or vehicle for one month and autopsied on day 31.

One day before autopsy, the animals were shifted to metabolic cage for acclaimatization for 24 h with food and water. Post acclaimatization animals were further left in metabolic cage for 24 h with water but no food. Blood and urine samples were collected after 24 h. Various biochemical parameters like serum calcium, serum phosphorus, serum osteocalcin, serum alkaline phosphatase (ALP) were evaluated. The animals were autopsied on day 31 and lumbar vertebrae, femur and tibia bones were isolated, cleaned and fixed in 70% ethanol in saline and stored at 4° C. until BMD measurement.

Initial and final body weight and uterine weight at autopsy were recorded. BMD measurements of region of interest (lumbar: global, L1-L4; femur: global, neck and mid-shaft; tibia: global, proximal and tibio-fibula junction point) was performed using a bone densitometer (Model 4500 Elite, Hologic) fitted with commercially available software (QDR 4500 ACCLAIM series) for a fan-beam DXA system that permits determination of bone densitometry and measurement of body composition in small animals in vivo.

Results:

There was a significant increase in BMD in 10 mg/kg dose for S006-1709 and in both doses of 1.0 and 5.0 mg/kg in Femur and Tibia for S007-1500.

TABLE 2

Change in BMD in comparison with control Sham intact

| Group | Femur | | | Tibia | | | Lumber Vertebra | | | | |
|---|---|---|---|---|---|---|---|---|---|---|---|
| | Global | Neck | Shaft | Global | Head | TFSP | Global | LV1 | LV2 | LV3 | LV4 |
| Vehicle | 100 | 100 | 100 | 100 | 100 | 100 | 100 | 100 | 100 | 100 | 100 |
| S006-1709 10 mg/kg | 138.75 *** | 141 *** | 167 *** | 133 *** | 115 | 124 *** | 120 * | 126 ** | 124 * | 90.3 | 125 |

(*** $p < 0.001$,
** $p < 0.01$,
* $p < 0.05$ when compared with the BMD of sham).

TABLE 3

| Compound code | FEMUR | | | TIBIA | | | LUMBER VERTEBRAE | | | | |
|---|---|---|---|---|---|---|---|---|---|---|---|
| Daily dose (mg/Kg) | Global | Neck | Mid-shaft | Global | Proximal | TFSP | Global | L-1 | L-2 | L-3 | L-4 |
| S007-1500 (1 mg/kg) | +27% * | +16% * | +35% * | +35% ** | +16.5% * | +70% *** | +13% * | +6% | +21% | +5.5% | -8.5% |
| S007-1500 (5 mg/kg) | +25% * | +26% * | +30% * | +37% ** | +33% ** | +69% *** | +17% | +7% | +14.5% | +25% | +14% |

Data indicates % increase versus vehicle control
(*** $p < 0.001$,
** $p < 0.01$,
* $p < 0.05$ when compared with the BMD of sham)

Pharmacokinetic Studies:

The pharmacokinetic evaluations of the compound S006-1709 of the present invention were carried out in experimental animals and the data (Table 4) and detailed procedures are described below:

In-vivo pharmacokinetic parameters were generated in Sprague Dawley rats at a dose of 5 mg/kg by oral route of administration. The blood samples were drawn at 0.25, 0.5, 0.75, 1.0, 1.5, 2.0, 2.5, 4.0, 6, 8, 10, 12, 18, 24, 28, 36 and 48 hours, processed and analyzed by Liquid Chromatography-Mass Spectrometry (LC-MS). Plasma concentration at different time points were plotted to give Plasma Concentration Time Profile and the data was fitted non-compartmentally using Win NonLin 5.1 version software and the estimates of pharmacokinetic parameters were derived with SD mean values. Maximum plasma concentration ($C_{max}$), time to achieve maximum plasma concentration ($t_{max}$), Area under curve (AUC), elimination half life ($T_{1/2}$) and mean residence time (MRT) were found to be 17.533±1.76, 15 min, 32.12±12.0 hr.ng/ml, 2.5 hr and 3.5 hr respectively.

TABLE 4

Pharmacokinetic estimates of S006-1709 in SD rats at a oral dose of 5 mg/kg

| PK Parameters | S006-1709 in SD rats at a oral dose of 5 mg/kg in SD rats |
|---|---|
| $C_{max}$ | 17.533 ± 1.76 |
| $t_{max}$ | 15 min |
| AUC | 32.12 ± 12.0 |
| $T_{1/2}$ | 2.5 h |
| MRT | 3.5 h |

We claim:

1. Substituted benzfurochromenes having the general formula I, and salts and chiral or achiral compounds thereof;

General formula I

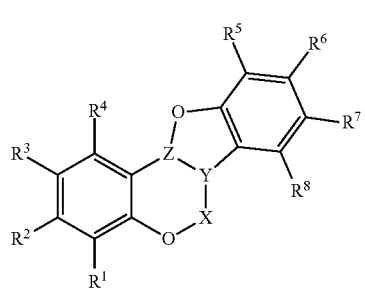

wherein $R^1$, $R^3$, $R^4$, $R^5$, $R^6$, $R^7$, and $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles, esters, hydroxy, mercapto, carbontrifluoride and nitro;

$R^2$ is independently selected from the group consisting of hydrogen, optionally substituted alkyl, optionally substituted alkenyl, optionally substituted alkoxyl, optionally substituted aryl, optionally substituted heteroaryl, optionally substituted optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, nitriles esters, mercapto, carbontrifluoride, and nitro;

wherein $R^1R^2$ or $R^2R^3$ or $R^6R^7$ may be connected and form either a five membered ring or a six membered ring selected from the group consisting of substituted furan, unsubstituted furan, substituted dihydrofuran, unsubstituted dihydrofuran, substituted pyran and unsubstituted pyran, or may be connected through a methylenedioxy moiety;

wherein X is selected from the units consisting of a ketone group, optionally substituted methylene group, and optionally substituted alkene; and wherein Y and Z is selected from the units consisting of CH, C—OH, C-Me, and C—OMe with the proviso that bond between Y and Z is a single bond.

2. A compound selected from the group consisting of:
i. 3-Allyloxy-4-methyl-6a,11a-dihydro-6H-benzo[4,5]furo[3,2-c]chromene
ii. 4-Methyl-6a,11a-dihydro-6H-benzo[4,5]furo[3,2-c]chromen-3-ol
iii. (4-Methyl-6a,11a-dihydro-6H-benzo[4,5]furo[3,2-c]chromen-3-yloxy)-acetonitrile
iv. 3-isopropoxy-6a,11a-dihydro-6H-benzofuro[3,2-c]chromene
v. 3-(allyloxy)-6a,11a-dihydro-6H-benzofuro[3,2-c]chromene and
vi. 1-(2-6a,11a-dihydro-6H-benzofuro[3,2-c]chromen-3-yloxy)ethyl)piperidine.

3. A method of treating osteoporosis; bone loss; bone formation; bone formation during Type-II/age related/senile osteoporosis, period of development and growth to attain higher peak bone mass, or bone fracture healing
comprising administering a pharmaceutically effective amount of a compound of claim 1 to a subject in need thereof.

4. A process of preparing substituted benzfurochromenes having the general formula I, salt and chirally pure compounds thereof as claimed in claim 1 comprising:
i. reacting compound having general formula A

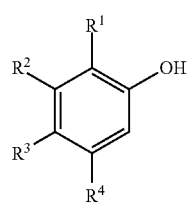

A with substituted 2'-methoxyphenyl acetic acid of formula B

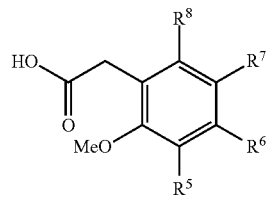

B in the presence of Lewis acid at a temperature ranging between 25° C. to 150° C. for a period ranging between 1 hr to 20 hr, wherein the substituents $R^1, R^2, R^3, R^4, R^5, R^6, R^7$, and $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride and nitro; and ii. isolating the compound of general formula C

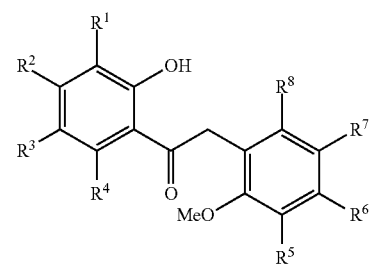

C and purifying the compound of formula C by chromatographic techniques;

iii. reacting the compound of general formula C with methanesulfonyl chloride in the presence of acidic medium and heating at a temperature ranging between 25° C. to 100° C. for a period ranging between 1 to 10 hr, iv. isolating the compound of general formula D

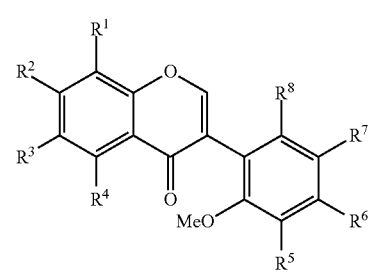

D wherein the substituents $R^1, R^2, R^3, R^4, R^5, R^6, R^7$, and $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride and nitro; and purifying the compound of formula D by chromatographic techniques;

v. reacting the compound of general formula D with either boron tribromide or aluminium trichloride in protic or aprotic solvents selected from the group consisting of THF, DMF, ethanol, acetonitrile and dichloromethane at a temperature ranging between −40° C. to 150° C. for a period ranging between 1 to 20 hr, wherein the substituents $R^1$, $R^2$, $R^3$, $R^4$, $R^5$, $R^6$, $R^7$, and $R^8$ are independently selected from the groups consisting of hydrogen, optionally substituted alkyl, optionally substituted alkenyl, optionally substituted alkoxyl, optionally substituted aryl, optionally substituted heteroaryl, optionally substituted acylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride and nitro; and isolating and purifying the compound of formula E

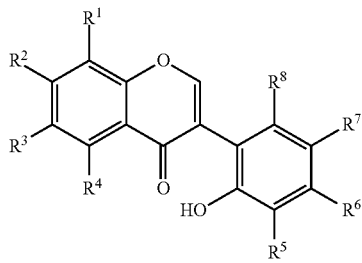

E by chromatographic techniques;

vi. reacting compound of general formula E with reducing agents with or without chiral catalysts or auxiliary in a protic or aprotic solvent at a temperature ranging between 0° C. to 150° C. for a period ranging between 1 to 20 hr, wherein the substituents $R^1$, $R^2$, $R^3$, $R^4$, $R^5$, $R^6$, $R^7$, and $R^8$ are independently selected from the groups consisting of hydrogen, independently selected from the groups consisting of hydrogen, optionally substituted alkyl, optionally substituted alkenyl, optionally substituted alkoxyl, optionally substituted aryl, optionally substituted heteroaryl, optionally substituted alkylthio, optionally substituted amino, optionally substituted acylamino, optionally substituted arylamino, optionally substituted acylthio, optionally substituted acyl, optionally substituted aroyl, optionally substituted acyloxy, optionally substituted thioamido, halogens, esters, hydroxy, mercapto, carbontrifluoride and nitro; and isolating and purifying the compound of formula F

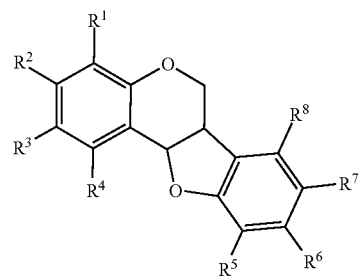

F by chromatographic techniques; and vii. resolving the chirally pure compounds from the racemic compounds of formula F by chiral HPLC techniques using chiral stationary phase in normal or reverse phase conditions.

5. The process of claim 4 further comprising converting compounds of formula F to pharmaceutically acceptable salts selected from the group consisting of: hydrochloride, formate, acetate, phenyl acetate, trifluoroacetate, acrylate, ascorbate, benzoate, chlorobenzoates, bromobenzoates, iodobenzoates, nitrobenzoates, hydroxybenzoates, alkylbenzoates, alkyloxybenzoates, alkoxycarbonylbenzoates, naphthalene-2 benzoate, butyrates, phenylbutyrates, hydroxybutyrates, caprate, caprylate, cinnamate, mandelate, mesylate, citrate, tartarate, fumarate, heptanoate, hippurate, lactate, malate, maleate, malonate, nicotinate, isonicotinate, oxalate, sodium, potassium, phthalate, terephthalate, phosphate, monohydrogen phosphate, dihydrogen phosphate, metaphosphate, pyrophosphate, propiolate, propionate, phenylpropionate, salicylate, sebate, succinate, suberate, sulphate, bisulphate, pyrosulphate, sulphite, bisulphate, sulphonate, benzene sulphonate, bromobenzene sulphonates, chlorobenzene sulphonates, ethane sulphonates, methane sulphonates, naphthalene sulphonates, and toluene sulphonates.

6. A pharmaceutical composition comprising at least one compound of claim 1 and optionally pharmaceutically acceptable carrier(s) or diluents(s) or excipient(s).

7. The composition as claimed in claim 6, wherein the pharmaceutical diluent is selected from the group consisting of lactose, mannitol, sorbitol, microcrystalline cellulose, sucrose, sodium citrate, and dicalcium phosphate.

8. The composition as claimed in claim 6 wherein the pharmaceutical excipient is selected from the group consisting gum tragacanth, gum acacia, methyl cellulose, gelatin, polyvinyl pyrrolidone, starch, agar-agar, calcium carbonate, sodium carbonate, silicates, alginic acid, corn starch, potato tapioca starch, primogel, magnesium stearate, calcium stearate or stearates, talc, solid polyethylene glycols, sodium lauryl sulphate, colloidal silicon dioxide, sucrose, saccharin, peppermint, methyl salicylate, orange flavor, vanilla flavor, cetyl alcohol, glyceryl monostearate, kaolin, bentonite clay, wax, paraffin and combinations thereof.

9. The composition as claimed in claim 6, wherein the effective dose of the composition is ranging between 0.1 to 5000 mg per kg body weight administered daily, bi-weekly, weekly or in more divided doses.

10. The composition as claimed in claim 6, wherein the composition is administered by the route selected from the group consisting of: oral, percutaneous, intramuscular, intraperitoneal, intravenous, and local.

11. The composition as claimed in claim 6, wherein the composition is used in the form of tablet, syrup, powder, capsule, suspension, solution, ointment, or mixture.

12. A method for prevention or treatment of diseases and syndromes caused by osteoporosis, bone loss, bone formation, bone fracture healing, and attainment of higher peak bone mass by administering a pharmaceutically effective amount of unsubstituted or substituted 6a,11a-dihydro-6H-benzo[4,5]furo[3,2-c]chromen-3-ol and salts, chiral or achiral compounds thereof to a subject in need thereof.

* * * * *

UNITED STATES PATENT AND TRADEMARK OFFICE
CERTIFICATE OF CORRECTION

PATENT NO.         : 8,686,028 B2
APPLICATION NO. : 13/127913
DATED              : April 1, 2014
INVENTOR(S)        : Goel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 106 days.

Signed and Sealed this
Thirtieth Day of May, 2017

Michelle K. Lee
*Director of the United States Patent and Trademark Office*